(12) United States Patent
Kleemann et al.

(10) Patent No.: US 6,436,999 B1
(45) Date of Patent: Aug. 20, 2002

(54) DIACYL-SUBSTITUTED GUANIDINES, A PROCESS FOR THEIR PREPARATION, THEIR USE AS MEDICINE OR DIAGNOSTIC AID, AND MEDICINE CONTAINING THEM

(75) Inventors: Heinz-Werner Kleemann, Bad Homburg; Hans-Jochen Lang, Hofheim; Andreas Weichert, Egelsbach; Peter Crause, Offenbach; Wolfgang Scholz, Eschborn; Udo Albus, Florstadt; Jan-Robert Schwark, Frankfurt, all of (DE)

(73) Assignee: Hoechst Aktiengesellschaft, Frankfurt am Main (DE)

( * ) Notice: Subject to any disclaimer, the term of this patent is extended or adjusted under 35 U.S.C. 154(b) by 0 days.

(21) Appl. No.: 08/837,460

(22) Filed: Apr. 18, 1997

Related U.S. Application Data

(63) Continuation of application No. 08/293,542, filed on Aug. 22, 1994, now abandoned.

(30) Foreign Application Priority Data

Aug. 24, 1993 (DE) .......................................... 43 28 352

(51) Int. Cl.$^7$ ..................... A01N 32/52; A01N 31/155; C07C 277/08; C07C 279/10
(52) U.S. Cl. ..................... 514/634; 514/311; 514/331; 514/351; 514/397; 514/399; 514/427; 514/428; 514/594; 546/168; 546/169; 546/175; 546/231; 546/332; 548/313.7; 548/314.4; 548/340.1; 548/561; 548/566; 564/50; 564/51; 564/225; 564/230; 564/237
(58) Field of Search ................ 564/152, 154, 564/50, 51, 225, 230, 237; 514/311, 331, 351, 397, 399, 427, 428, 594, 634; 546/168, 169, 175, 231, 332; 548/313.7, 314.4, 340.1, 561, 566

(56) References Cited

U.S. PATENT DOCUMENTS

| | | | |
|---|---|---|---|
| 4,225,613 A | 9/1980 | Ward | |
| 4,544,670 A | 10/1985 | Studt et al. | |
| 5,091,394 A | 2/1992 | Englert et al. | |
| 5,292,755 A | 3/1994 | Englert et al. | |
| 5,591,754 A | 1/1997 | Lang et al. | |

FOREIGN PATENT DOCUMENTS

| | | |
|---|---|---|
| CA | 2089440 A | 8/1993 |
| CA | 2112194 A | 6/1994 |
| EP | 0416499 A | 3/1991 |
| EP | 0556673 A | 8/1993 |
| EP | 0589336 A | 3/1994 |
| EP | 0604852 A | 7/1994 |
| WO | WO8400875 A | 3/1984 |

OTHER PUBLICATIONS

Database CAPLUS on STN, Acc. No. 1982:47082, Nakae, 'Synthesis of N,N'–dibenzoylguanidine and its convulsive action.' Neurosciences (Kobe, Jpn.) (1981), 7(Suppl. 2), pp. 205–217. abstract.*
CA62:1763(g), Jan. 1965.*
Internal Medicine, 4$^{th}$ Edition, Editor–in–Chief Jay Stein, pp. 699–715.*
Malik et al., "Bis–alkylaminoacyl Guanidines: Insect Repellants", Chemical Abstracts, vol. 107, No. 13 (1987), Abstract No. 111059y.
Krug et al., "Guanidine Derivatives. II. Methods of Synthesis of Acylguanidines", Chemical Abstracts, vol. 68, No. 7 (1968), Abstract No. 30007d.

* cited by examiner

Primary Examiner—Brian J. Davis
(74) Attorney, Agent, or Firm—Finnegan, Henderson, Farabow, Garrett & Dunner, LLP

(57) ABSTRACT

Diacyl-substituted guanidines of the formula I

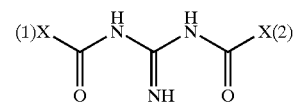

are described where X(1) and X(2) are

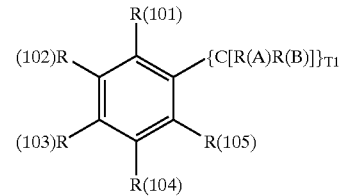

as defined herein. The compounds are suitable for use as antiarrhythmic pharmaceuticals possessing a cardioprotective component for the prophylaxis and treatment of infarction and for the treatment of angina pectoris, in connection with which they also inhibit or strongly reduce, in a preventitive manner the pathophysiological processes associated with the genesis of ischemically induced damage, in particular associated with the elicitation of ischemically induced cardiac arrhythmias.

19 Claims, No Drawings

DIACYL-SUBSTITUTED GUANIDINES, A PROCESS FOR THEIR PREPARATION, THEIR USE AS MEDICINE OR DIAGNOSTIC AID, AND MEDICINE CONTAINING THEM

This application is a continuation of prior application Ser. No. 08/293.542 filed Aug. 22, 1994, now abandoned.

The invention relates to diacyl-substituted guanidines of the formula I

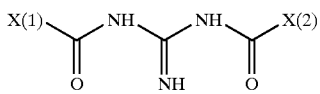

in which:

X(1) and X(2) are

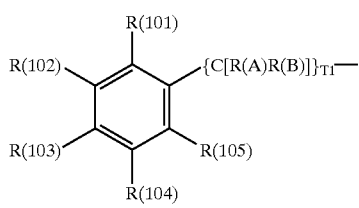

T1 is zero, 1, 2, 3 or 4,

R(A) and R(B) are, independently,
  hydrogen, F, Cl, Br, I, CN, OR(106), $(C_1-C_8)$-alkyl, $(C_3-C_8)$-cycloalkyl, $O_{zk}(CH_2)_{zl}C_{zm}F_{2zm+1}$, NR(107)R(108), phenyl or benzyl,
  where the aromatic radicals are not substituted or are substituted by 1–3 substituents selected from the group consisting of F, Cl, $CF_3$, methyl, methoxy and NR(109)R(110),
  R(109) and R(110) being
    hydrogen, $(C_1-C_4)$-alkyl or $(C_1-C_4)$-perfluoroalkyl,
zl is zero, 1, 2, 3 or 4,
zk is zero or 1,
zm is 1, 2, 3, 4, 5, 6, 7 or 8,
R(106) is
  hydrogen, $(C_1-C_8)$-alkyl, $(C_1-C_8)$-perfluoroalkyl, $(C_3-C_8)$-alkenyl, $(C_3-C_8)$-cycloalkyl, phenyl or benzyl,
  where the aromatic radicals are not substituted or are substituted by 1–3 substituents selected from the group consisting of F, Cl, $CF_3$, methyl, methoxy and NR(111)R(112),
  R(111) and R(112) being
    hydrogen, $(C_1-C_4)$-alkyl or $(C_1-C_4)$-perfluoroalkyl,
R(107) and R(108) are, independently of each other, defined as R(106),
or
R(107) and R(108) are together 4 or 5 methylene groups of which one $CH_2$ group can be replaced by oxygen, S, NH, N—$CH_3$ or N-benzyl,
or
X(1) and X(2) are

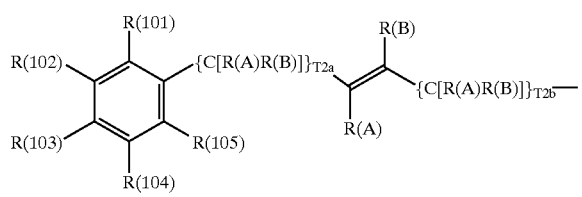

T2a and T2b are, independently of each other, zero, 1 or 2,
  where the double bond can have the E or Z configuration;
or
X(1) and X(2) are

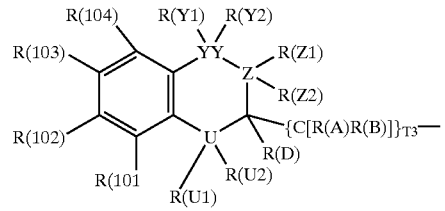

T3 is zero, 1 or 2,
U, YY and Z are, independently of each other,
  C or N,
  where U, YY and Z can carry the following number of substituents:

| U, YY or Z | Bonded to a double bond in the ring | Number of permitted substituents |
|---|---|---|
| C | yes | 1 |
| C | no | 2 |
| N | yes | 0 |
| N | no | 1 |

R(D) is hydrogen, $(C_1-C_8)$-alkyl or $(C_1-C_8)$-perfluoroalkyl, R(U1), R(U2), R(Y1), R(Y2), R(Z1) and R(Z2) are, independently of each other,
  hydrogen, F, Cl, Br, I, CN, OR(114), $(C_1-C_8)$-alkyl, $(C_3-C_8)$-cycloalkyl, $O_{zka}$ $(CH_2)_{zla}C_{zma}F_{2zma+1}$, NR(115)R(116), phenyl or benzyl,
  where the aromatic radicals are not substituted or are substituted by 1–3 substituents selected from the group consisting of F, Cl, $CF_3$, methyl, methoxy and NR(117)R(118),
  R(117) and R(118) being
    hydrogen, $(C_1-C_4)$-alkyl or $(C_1-C_4)$ perfluoroalkyl,
zka is zero or 1,
zla is zero, 1, 2, 3 or 4,
zma is 1, 2, 3, 4, 5, 6, 7 or 8,
R(114) is hydrogen, $(C_1-C_8)$-alkyl, $(C_1-C_8)$-perfluoroalkyl, $(C_3-C_8)$-alkenyl, $(C_3-C_8)$-cycloalkyl, phenyl or benzyl,
  where the aromatic radicals are not substituted or are substituted by 1–3 substituents selected from the group consisting of F, Cl, $CF_3$, methyl, methoxy and NR(119)R(120),
  R(119) and R(120) being
    hydrogen, $(C_1-C_4)$-alkyl or $(C_1-C_4)$-perfluoroalkyl,
R(115) and R(116) are, independently of each other, defined as R(114),
or
R(115) and R(116)
  are together 4 or 5 methylene groups of which one $CH_2$ group can be replaced by oxygen, S, NH, N—$CH_3$ or N-benzyl,
where, however, the constitution U is nitrogen (N), YY is nitrogen (N) and Z is carbon (C) is excepted,
R(101), R(102), R(103), R(104) and R(105) are, independently of each other, hydrogen, F, Cl, Br, I, —C≡N, $X_{zoa}$—$(CH_2)_{zpa}$—$(C_{zqa}F_{2zqa+1})$, R(110a)—$SO_{zbm}$, R(110b)R(110c)N—CO, R(111a)—CO— or R(112a)R(113a)N—$SO_2$—,
where the perfluoroalkyl group is straight-chain or branched, X is hydrogen, S or NR(114a), zoa is zero or 1, R(114a) being H or $(C_1-C_3)$-alkyl, zbm is zero, 1 or 2, zpa is zero, 1, 2, 3 or 4, zqa is 1, 2, 3, 4, 5, 6, 7 or 8, R(110a), R(110b), R(111a) and R(112a) are, independently, $(C_1-C_8)$-alkyl, $(C_3-C_8)$-alkenyl, —$C_{zn}H_{2zn}$—R(115a) or $(C_1-C_8)$-perfluoroalkyl, zn is zero, 1, 2, 3 or 4, R(115a) is $(C_3-C_8)$-cycloalkyl, phenyl, biphenylyl or naphthyl,
where the aromatic radicals are not substituted or are substituted by 1–3 substituents selected from the group consisting of F, Cl, $CF_3$, methyl, methoxy and NR(116a)R(117a),
R(116a) and R(117a) being
hydrogen, $(C_1-C_4)$-perfluoroalkyl or $(C_1-C_4)$-alkyl, or R(110b), R(111a) and R(112a) are also hydrogen, R(110c) and R(113a) are, independently, hydrogen, $(C_1-C_4)$-perfluoroalkyl or $(C_1-C_4)$-alkyl, or R(110b) and R(110c) and also R(112a) and R(113a) are together 4 or 5 methylene groups, of which one $CH_2$ group can be replaced by oxygen, sulfur, NH, N—$CH_3$ or N-benzyl, or R(101), R(102), R(103), R(104) and R(105) are, independently of each other, $(C_1-C_8)$-alkyl, —$C_{za}H_{2zal}$R(118a) or $(C_3-C_8)$-alkenyl, zal is zero, 1, 2, 3 or 4, R(118a) is $(C_3-C_8)$-cycloalkyl, phenyl, biphenylyl or naphthyl,
where the aromatic radicals are not substituted or are substituted by 1–3 substituents from the group consisting of F, Cl, $CF_3$, methyl, methoxy or NR(119a)R(119b),
R(119a) and R(119b) being
hydrogen, $(C_1-C_4)$-alkyl or $(C_1-C_4)$-perfluoroalkyl, or R(101), R(102), R(103), R(104) and R(105) are, independently of each other, $(C_1-C_9)$-heteroaryl which is linked via C or N and which is unsubstituted or is substituted by 1–3 substituents from the group consisting of F, Cl, $CF_3$, $CH_3$, methoxy, hydroxyl, amino, methylamino and dimethylamino, or R(101), R(102), R(103), R(104) and R(105) are, independently of each other,

—C≡C—R(193),

R(193) is phenyl which is not substituted or is substituted by 1–3 substituents from the group consisting of F, Cl, $CF_3$, methyl, methoxy or NR(194)R(195), R(194) and R(195) being
hydrogen or $CH_3$, or R(101), R(102), R(103), R(104) and R(105) are, independently of each other, —Y-para-$C_6H_4$—$(CO)_{zh}$—$(CHOH)_{zi}$—$(CH_2)_{zj}$—$(CHOH)_{zk}$—R(123), —Y-meta-$C_6H_4$—$(CO)_{zad}$—$(CHOH)_{zae}$—$(CH_2)_{zaf}$—$(CHOH)_{zag}$—R(124)

or

—Y-ortho-$C_6H_4$—$(CO)_{zah}$—$(CHOH)_{zao}$—$(CH_2)_{zap}$—$(CHOH)_{zak}$—R(125), Y is oxygen, —S— or —NR(122d)—, zh, zad and zah are, independently, zero or 1, zi, zj, zk, zae, zaf, zag, zao, zap and zak are, independently, zero, 1, 2, 3 or 4, where, however, in each case, zh, zi and zk are not simultaneously zero, zad, zae and zag are not simultaneously zero and zah, zao and zak are not simultaneously zero, R(123), R(124) R(125) and R(122d) are, independently, hydrogen or $(C_1-C_3)$-alkyl, or R(101), R(102), R(103), R(104) and R(105) are, independently of each other, SR(129), —OR(130), —NR(131)R(132) or —CR(133)—R(134)R(135), R(129), R(130), R(131) and R(133), are, independently, —$C_{zab}H_{2zab}$—$(C_1-C_9)$-heteroaryl which is unsubstituted or is substituted by 1–3 substituents from the group consisting of F, Cl, $CF_3$, $CH_3$, methoxy, hydroxyl, amino, methylamino and dimethylamino, zab is zero, 1 or 2, R(132), R(134) and R(135) are, independently of each other, defined as R(129), or hydrogen, $(C_1-C_4)$-alkyl or $(C_1-C_4)$-perfluoroalkyl, or R(101), R(102), R(103), R(104) and R(105) are, independently of each other, —W-para-$(C_6H_4)$—R(196), —W-meta-$(C_6H_4)$—R(197) or —W-ortho-$(C_6H_4)$—R(198), R(196), R(197) and R(198) are, independently, $(C_1-C_9)$-heteroaryl which is linked via C or N and which is unsubstituted or is substituted by 1 to 3 substituents from the group consisting of F, Cl, $CF_3$, $CH_3$, methoxy, hydroxyl, amino, methylamino, dimethylamino and benzyl, W is oxygen, S or NR(136)—, R(136) being hydrogen or $(C_1-C_4)$-alkyl, or R(101), R(102), R(103), R(104) and R(105) are, independently of each other, R(146)X(1a)—, X(1a) is oxygen, S, NR(147), (D=O)A— or NR(148)C=MN$^{(*)}$R(149)—, M is oxygen or sulfur, A is oxygen or NR(150), and D is C or SO, R(146) is $(C_1-C_8)$-alkyl, $(C_3-C_8)$-alkenyl, $(CH_2)_{zbz}C_{zdz}F_{2zdz+1}$ or $-C_{zxa}H_{2zxa}-R(151)$,
zbz is zero or 1,
zdz is 1, 2, 3, 4, 5, 6 or 7,
zxa is zero, 1, 2, 3 or 4,
R(151) is
  $(C_3-C_8)$-cycloalkyl, phenyl, biphenylyl or naphthyl, where the aromatic radicals are not substituted or are substituted by 1–3 substituents from the group consisting of F, Cl, $CF_3$, methyl, methoxy and NR(152)R(153),
  R(152) and R(153) being
    hydrogen, $(C_1-C_4)$-alkyl or $(C_1-C_4)$-perfluoroalkyl,
  R(147), R(148) and R(150) are, independently, hydrogen, $(C_1-C_4)$-alkyl or $(C_1-C_4)$-perfluoroalkyl,
  R(149) is defined as R(146),
or
R(146) and R(147), or R(146) and R(148), respectively, are together 4 or 5 methylene groups of which one $CH_2$ group can be replaced by oxygen, sulfur, NH, N—$CH_3$ or N-benzyl, where A and N(*) are bonded to the phenyl nucleus of the alkanoyl parent substance,
or
R(101), R(102), R(103), R(104) and R(105) are, independently of each other,
  —SR(164), —OR(165), —NHR(166), —NR(167)R(168), —CHR(169)R(170),
  —CR(154)R(155)OH, —C≡CR(156), —CR(158)=CR(157) or —[CR(159)R(160)]$_{zu}$—(C=O)—[CR(161)R(162)]$_{zv}$—R(163),
  R(164), R(165), R(166), R(167) and R(169) are identical or different and are
    —$(CH_2)_{zy}$—$(CHOH)_{zz}$—$(CH_2)_{zaa}$—$(CHOH)_{zt}$—R(171) or —$(CH_2)_{zab}$—O—$(CH_2-CH_2O)_{zac}$—R(172),
    R(171) and R(172) being
      hydrogen or methyl,
    zu is 1, 2, 3 or 4,
    zv is zero, 1, 2, 3 or 4,
    zy, zz, zaa, zab and zac are identical or different and are
      zero, 1, 2, 3 or 4,
    zt is 1, 2, 3 or 4,
  R(168), R(170), R(154) and R(155) are identical or different and are
    hydrogen or $(C_1-C_6)$-alkyl,
  or
  R(169) and R(170), or R(154) and R(155), respectively, are, together with the carbon atom carrying them, a $(C_3-C_8)$-cycloalkyl,
  R(163)
    is hydrogen, $(C_1-C_6)$-alkyl, $(C_3-C_8)$-cycloalkyl or —$C_{zeb}H_{2zeb}$—R(173),
    zeb is zero, 1, 2, 3 or 4,
  R(156), R(157) and R(173) are, independently, phenyl which is unsubstituted or is substituted by 1–3 substituents from the group consisting of F, Cl, $CF_3$, methyl, methoxy and NR(174)R(175),
    R(174) and R(175) being
      hydrogen or $(C_1-C_4)$-alkyl,
  or
  R(156), R(157) and R(173) are, independently, $(C_1-C_9)$-heteroaryl which is unsubstituted or is substituted as phenyl,
  R(158), R(159), R(160), R(161) and R(162) are hydrogen or methyl, or
R(101), R(102), R(103), R(104) and R(105) are, independently of each other,
  R(176)—NH—$SO_2$—,
  R(176) is R(177)R(178)N—(C=Y')—,
  Y' is oxygen, S or N—R(179),
  R(177) and R(178) are identical or different and are
    hydrogen, $(C_1-C_8)$-alkyl, $(C_3-C_6)$-alkenyl or —$C_{zfa}H_{2zfa}$—R(180),
    zfa is zero, 1, 2, 3 or 4,
    R(180) is $(C_5-C_7)$-cycloalkyl or phenyl which is unsubstituted or substituted by 1–3 substituents from the group consisting of F, Cl,
  or
  R(177) and R(178)
    are together 4 or 5 methylene groups of which one $CH_2$ group can be replaced by oxygen, sulfur, NH, N—$CH_3$ or N-benzyl,
  R(179) is defined as R(177) or is amidine,
or
R(101), R(102), R(103), R(104) and R(105) are, independently of each other,
  NR(184a)R(185), OR(184b), SR(184c) or —$C_{znx}H_{2znx}$—R(184d),
  znx is zero, 1, 2, 3 or 4,
  R(184d)
    is $(C_3-C_7)$-cycloalkyl or phenyl which is not substituted or is substituted by 1–3 substituents from the group consisting of F, Cl, $CF_3$, methyl, methoxy and NR(116k)R(117k),
    R(116k) and R(117k) being
      hydrogen or $(C_1-C_4)$-alkyl,
  R(184a), R(184b), R(184c) and R(185) are, independently of each other,
    hydrogen, $(C_1-C_8)$-alkyl, $(C_1-C_8)$-perfluoroalkyl or $(CH_2)_{zao}$—R(184g),
    zao is zero, 1, 2, 3 or 4,
    184g is $(C_3-C_7)$-cycloalkyl or phenyl which is not substituted or is substituted by 1–3 substituents from the group consisting of F, Cl, $CF_3$, methyl, methoxy and NR(184u)R(184v),
    R(184u) and R(184v) being
      hydrogen or $(C_1-C_4)$-alkyl,
  or
  R(184a) and R(185) are together 4 or 5 methylene groups of which one $CH_2$ group can be replaced by oxygen, sulfur, NH, N—$CH_3$ or N-benzyl,
and also pharmaceutically tolerated salts thereof,
where, however, the following compounds are excepted:

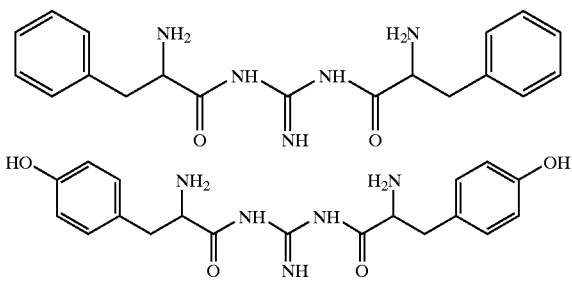

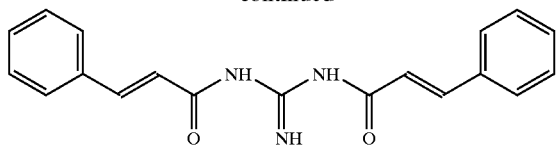

and where, additionally, the compounds are excepted in which the radicals R(1) to R(5) are combined as follows:

| R(101) [X(1)] | R(102) [X(1)] | R(103) [X(1)] | R(104) [X(1)] | R(105) [X(1)] | R(105) [X(2)] | R(104) [X(2)] | R(103) [X(2)] | R(102) [X(2)] | R(101) [X(2)] |
|---|---|---|---|---|---|---|---|---|---|
| H | Cl | Cl | H | H | H | H | Cl | Cl | H |
| H | H | NH₂ | H | H | H | H | NH₂ | H | H |
| H | H | H | H | H | H | H | H | H | H |
| Cl | H | H | H | H | H | H | H | H | Cl |
| H | H | Cl | H | H | H | H | Cl | H | H |
| H | H | CH₃ | H | H | H | H | CH₃ | H | H |
| H | H | NH₂ | H | H | H | H | H | H | H |
| H | H | Cl | H | H | H | H | H | H | H |
| H | H | CH₃ | H | H | H | H | H | H | H |

Compounds of the formula I are preferred in which X(1) is the same as X(2) and in which the other substituents are as defined above.

Compounds of the formula I are particularly preferred in which:

X(1) and X(2) are

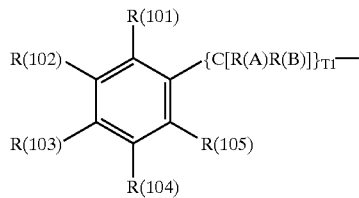

T1 is zero or 2,

R(A) and R(B) are, independently, hydrogen, F, Cl, CN, OR(106), (C₁–C₄)-alkyl, (C₅–C₆)-cycloalkyl, CF₃ or NR(107)R(108),

R(106)

is hydrogen, (C₁–C₄)-alkyl, CF₃, phenyl or benzyl, where the aromatic radicals are not substituted or are substituted by 1–3 substituents selected from the group consisting of F, Cl, CF₃, methyl, methoxy and NR(111)R(112), R(111) and R(112) being hydrogen, CH₃ or CF₃, R(107) and R(108) are, independently of each other, defined as R(106), or R(107) and R(108) are together 4 or 5 methylene groups of which one CH₂ group can be replaced by oxygen, S, NH, N—CH₃ or N-benzyl, or X(1) is

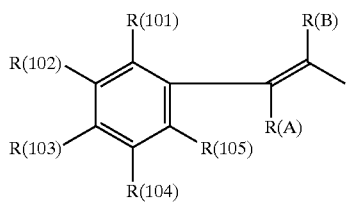

where the double bond can be in the E or Z configuration, or

X(1) is

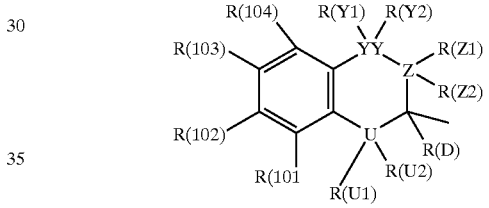

U, YY and Z are, independently of each other,

C or N;

with, however, the restriction that only one of the positions U, YY and Z can be nitrogen;

where

U, YY and Z can carry the following number of substituents:

| U, YY or Z | Bonded to a double bond in the ring | Number or permitted substituents |
|---|---|---|
| C | yes | 1 |
| C | no | 2 |
| N | yes | 0 |
| N | no | 1 |

R(D) is hydrogen,

R(U1), R(U2), R(Y1), R(Y2), R(Z1) and R(Z2) are, independently of each other, hydrogen, F, Cl, CN, OR(114), CH₃, CF₃ or NR(115)R(116),

R(114)

is hydrogen, (C₁–C₄)-alkyl, CF₃, phenyl or benzyl, where the aromatic radicals are not substituted or are substituted by 1–3 substituents selected from the group consisting of F, Cl, CF₃, methyl, methoxy and NR(119)R(120), R(119) and R(120) being hydrogen, $CH_3$ or $CF_3$, R(115) and R(116) are, independently of each other, defined as R(114), or R(115) and R(116)
are together 4 or 5 methylene groups of which one $CH_2$ group can be replaced by oxygen, S, NH, N—$CH_3$ or N-benzyl, R(101)
is hydrogen, F, Cl, $CH_3$, OH, $NH_2$ or $CF_3$, R(102)
is hydrogen, F, Cl, Br, —C≡N, —$C_{zqa}F_{2zqa}CF_3$, R(110a)—$SO_2$, R(110b)R(110c)N—CO—, R(111a)—CO— or R(112a) R(113a) N—$SO_2$—, R(115a), R(110b), R(111a) and R(112a) are, independently,
($C_1$–$C_4$)-alkyl, ($C_3$–$C_4$)-alkenyl, —$C_{zn}H_{2zn-R(}115a)$ or $CF_3$, zn is zero or 1, zqa is zero, 1, 2, 3, 4 or 5, R(115a)
is ($C_3$–$C_6$)-cycloalkyl or phenyl
which is not substituted or is substituted by 1–2 substituents from the group consisting of F, Cl, $CF_3$, methyl, methoxy and NR(116a)R(117a),
R(116a) and R(117a)
being hydrogen or methyl, or R(110b), R(111a) and R(112a) are also hydrogen,
R(110c) and R(113a) are, independently, hydrogen or methyl, R(103)
is —Y-para-$C_6H_4$—$(CO)_{zh}$—$(CHOH)_{zi}$—$(CH_2)_{zj}$—$(CHOH)_{zk}$—R(123),
—Y-meta-$C_6H_4$—$(CO)_{zad}$—$(CHOH)_{zae}$—$(CH_2)_{zaf}$—$(CHOH)_{zag}$—R(124) or
—Y-ortho-$C_6H_4$—$(CO)_{zah}$—$(CHOH)_{zao}$—$(CH_2)_{zap}$—$(CHOH)_{zak}$—R(125), Y is oxygen, S or —NR(83), R(123), R(124), R(125) and R(83) are, independently, hydrogen or methyl, zh, zad and zah are, independently,
zero or 1, zi, zk, zae, zag, zao and zak are, independently,
zero, 1, 2 or 3, zj, zaf and zap are, independently,
zero or 1, where, however, in each case, zh, zi and zk are not simultaneously zero,
zad, zae and zag are not simultaneously zero and
zah, zao and zak are not simultaneously zero, or R(103) is hydrogen, F, Cl, Br, CN, ($C_1$–$C_8$)-alkyl, $CF_3$, ($C_3$–$C_8$)-alkenyl or —$C_{zal}H_{2zal}$R(118a), zal is zero, 1 or 2, R(118a) is ($C_3$–$C_6$)-cycloalkyl or phenyl
which is not substituted or is substituted by 1–2 substituents selected from the group consisting of F, Cl, $CF_3$, methyl, methoxy and NR(119a)R(119b),
R(119a) and R(119b) being
hydrogen or $CH_3$, or R(103)
is ($C_1$–$C_9$)-heteroaryl
which is linked via C or N and which is unsubstituted or is substituted by 1–2 substituents from the group consisting of F, Cl, $CF_3$, $CH_3$, methoxy, hydroxyl, amino, methylamino and dimethylamino, or R(103)
is —W-para-$(C_6H_4)$—R(196), —W-meta-$(C_6H_4)$—R(197) or —W-ortho-$(C_6H_4)$—R(198), R(196), R(197) and R(198) are, independently, pyrrolyl, imidazolyl, pyrazolyl or pyridyl
which in each case is unsubstituted or substituted by 1 to 2 radicals selected from the group consisting of F, Cl, $CF_3$, $CH_3$, methoxy, dimethylamino and benzyl, W is oxygen, —S— or NR(136)—, R(136) being hydrogen or methyl, or R(103) is
—SR(129), —OR(130), —NR(131)R(132) or —CR(133)R(134)R(135), R(129), R(130), R(131) and R(133) are, independently of each other,
—$C_{zab}H_{2zab}$—($C_1$–$C_9$)-heteroaryl
which is unsubstituted or substituted by 1–2 substituents selected from the group consisting of F, Cl, $CF_3$, $CH_3$, methoxy, hydroxyl, amino, methylamino and dimethylamino, zab is zero or 1, R(132), R(134) and R(135) are, independently of each other,
hydrogen or $CH_3$, or R(103) is
R(110a)—$SO_2$ or R(112a)R(113a)N—$SO_2$—, R(110a) is
($C_1$–$C_4$)—alkyl, $CF_3$, ($C_3$–$C_4$)—alkenyl or —$C_{zn}H_{2zn}$—R(115a), zn is zero or 1, R(115a) is
($C_3$–$C_6$)-cycloalkyl or phenyl
which is not substituted or is substituted by 1–2 substituents selected from the group consisting of F, Cl, $CF_3$, methyl, methoxy and NR(116a)R(117a),
R(116a) and R(117a) being
hydrogen or $CH_3$, R(112a) is
hydrogen, ($C_1$–$C_4$)-alkyl, $CF_3$, ($C_3$–$C_4$)-alkenyl or —$C_{za}H_{2za}$—R(115a), za is zero or 1, R(115a) is
($C_3$–$C_6$)-cycloalkyl or phenyl
which is not substituted or is substituted by 1–2 substituents selected from the group consisting of F, Cl, $CF_3$, methyl, methoxy and NR(116a)R(117a),
R(116a) and R(117a) being hydrogen or $CH_3$, R(113a) is
hydrogen or $CH_3$, or R(112a) and R(113a) are together 4 or 5 methylene groups of which one $CH_2$ group can be replaced by oxygen, S, NH, N—$CH_3$ or N-benzyl, or R(103) is R(146)X(1a)—, X(1a) is oxygen, S, NR(147), (C=O)A— or NR(148)C=MN$^{(*)}$R(149)—, M is oxygen, and A is oxygen or NR(150), R(146) and R(147) are, independently,
hydrogen, $(C_1-C_6)$-alkyl, $(C_3-C_4)$-alkenyl, $(CH_2)_{zbz}C_{zdz}F_{2zdz+1}$ or $C_{zxa}H_{2zxa}$—R(151), zbz is zero or 1, zdz is 1, 2, 3, 4, 5, 6 or 7, zxa is zero or 1, R(151)
is $(C_3-C_6)$-cycloalkyl or phenyl which is not substituted or is substituted by 1–2 substituents selected from the group consisting of F, Cl, $CF_3$, methyl, methoxy or NR(152)R(153), R(152) and R(153) being
hydrogen or $CH_3$, R(148)
is hydrogen or $(C_1-C_4)$-alkyl, R(149) is defined as R(146), or R(146) and R(147), or R(146) and R(148), respectively, are together 4 or 5 methylene groups of which one $CH_2$ group can be replaced by oxygen, S, NH, N—$CH_3$ or N-benzyl, where A and N$^{(*)}$ are bonded to the phenyl nucleus of the benzoylguanidine parent substance, or R(103)
is —SR(164), —OR(165), —NHR(166), —NR(167)R(168), —CHR(169)R(170), —[CR(154)R(155)OH], —C≡CR(156), —CR(158)=CR(157) or —[CR(159)R(160a)]$_{zu}$—(CO)—[CR(161)R(162)]$_{zv}$—R(163), R(164), R(165), R(166), R(167) and R(169) are identical or different and are
—(CH$_2$)$_{zy}$—(CHOH)$_{zz}$—(CH$_2$)$_{zaa}$—(CHOH)$_{zt}$—R(171) or —(CH$_2$)$_{zab}$—O—(CH$_2$—CH$_2$O)$_{zac}$—R(172), R(171) and R(172) are hydrogen or methyl, zu is 1 or 2, zv is zero, 1 or 2, zy, zz, zaa, zab and zac are identical or different and are zero, 1 or 2, zt is 1, 2 or 3, R(168), R(170), R(154) and R(155) are identical or different and are
hydrogen or methyl, or R(169) and R(170), or R(154) and R(155), respectively, together with the carbon atom carrying them, are a $(C_3-C_6)$-cycloalkyl, R(163) is
hydrogen, $(C_1-C_4)$-alkyl, $(C_3-C_6)$-cycloalkyl or —C$_{zeb}$H$_{2zeb}$—R(173), zeb is zero, 1 or 2, R(156), R(157) and R(173) are, independently of each other,
phenyl which is unsubstituted or is substituted by 1–2 substituents selected from the group consisting of F, Cl, $CF_3$, methyl, methoxy and NR(174)R(175), R(174) and R(175) being
hydrogen or $CH_3$, or R(156), R(157) and R(173) are, independently of each other,
$(C_1-C_9)$-heteroaryl which is unsubstituted or is substituted as phenyl, R(158), R(159), R(160), R(161) and R(162)
are hydrogen or methyl, or R(103)
is R(176)—NH—SO$_2$—, R(176)
is R(177)R(178)N—(C=Y')—, Y' is oxygen, S or N—R(179), R(177) and R(178) are identical or different and are
hydrogen, $(C_1-C_4)$-alkyl, $(C_3-C_4)$-alkenyl or —C$_{zfa}$H$_{2zfa}$—R(180), zfa is zero or 1, R(180)
is $(C_5-C_7)$-cycloalkyl or phenyl which is unsubstituted or substituted by 1–2 substituents selected from the group consisting of F, Cl, $CF_3$, methoxy or methyl, or R(177) and R(178) are together 4 or 5 methylene groups of which one $CH_2$ group can be replaced by oxygen, S, NH, N—$CH_3$ or N-benzyl, R(179) is defined as R(177), R(104)
is hydrogen, $CF_3$ $(C_1-C_8)$-alkyl or —C$_{zal}$H$_{2zal}$R(118a), zal is zero or 1, R(118a)
is $(C_3-C_6)$-cycloalkyl or phenyl which is not substituted or is substituted by 1–2 substituents selected from the group consisting of F, Cl, $CF_3$, methyl, methoxy and NR(119a)R(119b), R(119a) and R(119b) being hydrogen or $CH_3$, or R(104)
is quinolyl, isoquinolyl, pyrrolyl, pyridyl or imidazolyl which are linked via C or N and which are unsubstituted or substituted by 1–2 substituents selected from the group consisting of F, Cl, $CF_3$, $CH_3$, methoxy, hydroxyl, amino, methylamino and dimethylamino, or R(104)
is R(110a)—SO$_2$ or R(112a)R(113a)N—SO$_2$—, R(110a)
is $(C_1-C_4)$-alkyl or $CF_3$, R(112a)
is hydrogen, $(C_1-C_4)$-alkyl, $CF_3$ or —C$_{za}$H$_{2za}$—R(115a), za is zero or 1, R(115a)
is phenyl which is not substituted or is substituted by 1–2 substituents selected from the group consisting of F, Cl, $CF_3$, methyl, methoxy and NR(116a)R(117a), R(116a) and R(117a) being hydrogen or $CH_3$, R(113a)
is hydrogen or $CH_3$, or R(104)
is —C≡CR(193),
R(193)
is phenyl which is unsubstituted or substituted by 1–2 substituents selected from the group consisting of F, Cl, CF$_3$, methyl, methoxy and NR(194)R(195),
R(194) and R(195) being
hydrogen or CH$_3$,
R(105)
is hydrogen,
and also the pharmaceutically tolerated salts thereof.

Dibenzoylguanidines of the formula Ia
are likewise preferred
in which:

R(1), R(5), R(6) and R(10) are, independently of each other,

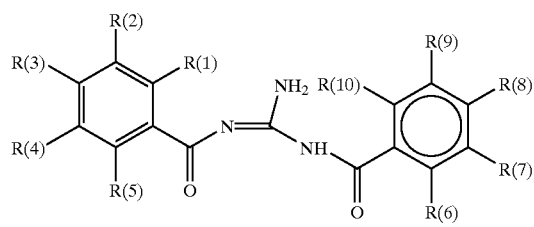
(Ia)

hydrogen, F, Cl, (C$_1$–C$_3$)-alkyl, —OR(11), C$_r$F$_{2r+1}$ or —NR(11)R(12),
R(11) and R(12) are, independently, hydrogen or (C$_1$–C$_3$)-alkyl,
r is from 1 to 4, R(2), R(4), R(7) and R(9) are, independently of each other,
hydrogen, F, Cl, Br, I, —C≡N, X$_o$—(CH$_2$)$_p$—(CF$_2$)$_q$—CF$_3$, R(13)—SO$_m$, R(14)R(15)N—CO—, R(16)—CO— or R(17)R(18)N—SO$_2$—,
X is oxygen, S or NR(19),
m is zero, 1 or 2,
o is zero or 1,
p is zero, 1 or 2,
q is zero, 1, 2, 3, 4, 5 or 6,
R(13), R(14), R(16) and R(17) are, independently, (C$_1$–C$_8$)-alkyl, (C$_3$–C$_6$)-alkenyl, —C$_n$H$_{2n}$—R(20) or CF$_3$,
n is zero, 1, 2, 3 or 4,
R(19) is hydrogen or (C$_1$–C$_3$)-alkyl,
R(20) is (C$_3$–C$_7$)-cycloalkyl or phenyl
which is not substituted or is substituted by 1–3 substituents from the group consisting of F, Cl, CF$_3$, methyl, methoxy or NR(21)R(22) with R(21) and R(22) being H or (C$_1$–C$_4$)-alkyl,
where R(14), R(16) and R(17) also have the meaning of H,
R(15) and R(18) are, independently,
hydrogen or (C$_1$–C$_4$)-alkyl,
where R(14) and R(15) and also R(17) and R(18) can together be 4 or 5 methylene groups of which one CH$_2$ group can be replaced by oxygen, S, NH, N—CH$_3$ or N-benzyl,
or
R(2), R(4), R(7) and R(9) are, independently of each other,
(C$_1$–C$_8$)-alkyl or —C$_{al}$H$_{2al}$R(84),
al is zero, 1 or 2,
R(84) is (C$_3$–C$_8$)-cycloalkyl or phenyl
which is not substituted or is substituted by 1–3 substituents from the group consisting of F, Cl, CF3, methyl, methoxy or NR(85)R(86), with R(85) and R(86) being hydrogen or CH$_3$; or
R(2), R(4), R(7) and R(9) are, independently of each other,
(C$_1$–C$_9$)-heteroaryl
which is linked via C or N and which is unsubstituted or is substituted by 1–3 substituents from the group consisting of F, Cl, CF$_3$, CH$_3$, methoxy, hydroxyl, amino, methylamino or dimethylamino; or
R(2), R(4), R(7) and R(9) are, independently of each other,
—C≡CR(93),
R(93) is phenyl
which is unsubstituted or is substituted by 1–3 substituents from the group consisting of F, Cl, CF$_3$, methyl, methoxy or NR(94)R(95), with R(94) and R(95) being hydrogen or CH$_3$;
R(3) and R(8) are, independently of each other, defined as R(2), or are

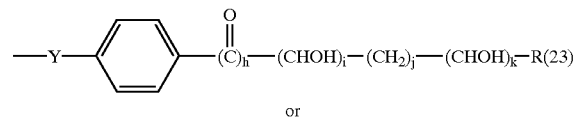

or

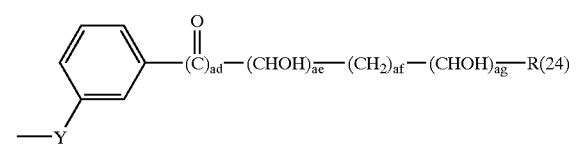

or

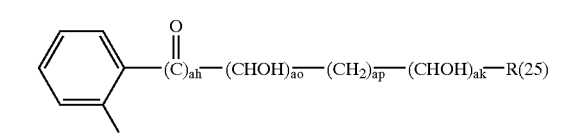

Y is oxygen, —S— or —NR(83)—,
h, ad and ah are, independently,
zero or 1,
i, j, k, ae, af, ag, ao, ap and ak are, independently,
zero, 1, 2, 3 or 4,
where, however, in each case, h, i and k are not simultaneously zero,
ad, ae and ag are not simultaneously zero and ah, ao and ak are not simultaneously zero,
R(23), R(24), R(25) and R(83) are, independently,
hydrogen or (C$_1$–C$_3$)-alkyl,
or
R(3) and R(8) are, independently of each other,
hydrogen, F, Cl, Br, I, CN, (C$_1$–C$_8$)-alkyl, (C$_1$–C$_8$)-perfluoroalkyl, (C$_3$–C$_8$)-alkenyl or —C$_g$H$_{2g}$R(26),
g is zero, 1, 2, 3 or 4,
R(26) is (C$_3$–C$_8$)-cycloalkyl, phenyl, biphenylyl or naphthyl,
where the aromatic radicals are not substituted or are substituted by 1–3 substituents from the group consisting of F, Cl, CF$_3$, methyl, methoxy or NR(27)R(28), with R(27) and R(28) being hydrogen, $(C_1-C_4)$-alkyl or $(C_1-C_4)$-perfluoroalkyl; or R(3) and R(8) are, independently of each other,
SR(29), —OR(30), —NR(31)R(32) or —CR(33)R(34)R(35);
R(29), R(30), R(31) and R(33) are, independently, —$C_aH_{2a}$—$(C_1-C_9)$-heteroaryl
which is unsubstituted or substituted by 1–3 substituents from the group consisting of F, Cl, $CF_3$, $CH_3$, methoxy, hydroxyl, amino, methylamino or dimethylamino,
a is zero, 1 or 2,
R(32), R(34) and R(35) are, independently of each other,
defined as R(29), or hydrogen, $(C_1-C_4)$-alkyl or $(C_1-C_4)$-perfluoroalkyl; or R(3) and R(8) are, independently of each other,

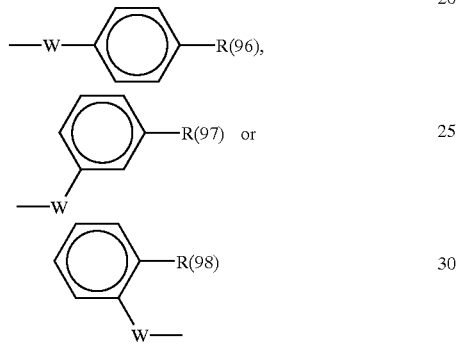

R(96), R(97) and R(98) are, independently, $(C_1-C_9)$-heteroaryl
which is linked via C or N and which is unsubstituted or is substituted by 1 to 3 substituents from the group consisting of F, Cl, $CF_3$, $CH_3$, methoxy, hydroxyl, amino, methylamino, dimethylamino or benzyl,
W is oxygen, S or NR(99)—,
R(99) is hydrogen or $(C_1-C_4)$-alkyl, or R(3) and R(8) are, independently of each other,
R(72)—$SO_m$ or R(73)R(74)N—$SO_2$—,
m is 1 or 2,
R(72) is $(C_1-C_8)$-alkyl, $(C_1-C_8)$-perfluoroalkyl, $(C_3-C_8)$-alkenyl or —$C_sH_{2s}$—R(75),
s is zero, 1, 2, 3 or 4,
R(75) is $(C_3-C_8)$-cycloalkyl, phenyl, biphenylyl or naphthyl,
where the aromatic radicals are not substituted or are substituted by 1–3 substituents from the group consisting of F, Cl, $CF_3$, methyl, methoxy or NR(76)R(77), with R(76) and R(77) being hydrogen, $(C_1-C_4)$-alkyl or $(C_1-C_4)$-perfluoroalkyl;
R(73) is hydrogen, $(C_1-C_8)$-alkyl, $(C_1-C_8)$-perfluoroalkyl, $(C_3-C_8)$-alkenyl or —$C_wCH_{2w}$—R(78),
w is zero, 1, 2, 3 or 4,
R(78) is $(C_3-C_8)$-cycloalkyl, phenyl, biphenylyl or naphthyl,
where the aromatic radicals are not substituted or are substituted by 1–3 substituents from the group consisting of F, Cl, $CF_3$, methyl, methoxy or NR(79)R(80), with R(79) and R(80) being hydrogen, $(C_1-C_4)$-alkyl or $(C_1-C_4)$-perfluoroalkyl,
R(74) is hydrogen, $(C_1-C_4)$-alkyl or $(C_1-C_4)$-perfluoroalkyl,
where R(73) and R(74) can together be 4 or 5 methylene groups of which one $CH_2$ group can be replaced by oxygen, S, NH, N—$CH_3$ or N-benzyl; or R(3) and R(8) are, independently of each other,
R(39)X—,
X is oxygen, S, NR(40), (D=O)A— or NR(41)C=MN$^{(*)}$R(42)—, with
M is oxygen or S,
A is oxygen or NR(43), and
D is C or SO,
R(39) is $(C_1-C_8)$-alkyl, $(C_3-C_8)$-alkenyl, $(CH_2)_bC_dF_{2d+1}$ or —$C_xH_{2x}$—R(44),
b is zero or 1,
d is 1, 2, 3, 4, 5, 6 or 7,
x is zero, 1, 2, 3 or 4,
R(44) is $(C_3-C_8)$-cycloalkyl, phenyl, biphenylyl or naphthyl,
where the aromatic radicals are not substituted or are substituted by 1–3 substituents from the group consisting of F, Cl, $CF_3$, methyl, methoxy or NR(45)R(46); with R(45) and R(46) being hydrogen, $(C_1-C_4)$-alkyl or $(C_1-C_4)$-perfluoroalkyl;
R(40), R(41) and R(43) are, independently, hydrogen, $(C_1-C_4)$-alkyl or $(C_1-C_4)$-perfluoroalkyl,
R(42) is defined as R(39), where
R(39) and R(40), or R(39) and R(41), respectively, can together be 4 or 5 methylene groups of which one $CH_2$ group can be replaced by oxygen, S, NH, N—$CH_3$ or N-benzyl, where
A and N$^{(*)}$ are bonded to the phenyl nucleus of the benzoylguanidine parent substance; or R(3) and R(8) are, independently of each other,
—SR(47), —OR(48), —NHR(49), —NR(50)R(51), —CHR(52)R(53),

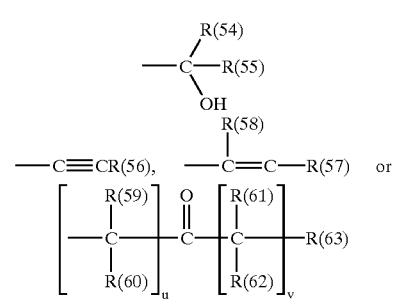

R(47), R(48), R(49), R(50) and R(52) are identical or different and are
—$(CH_2)_y$—$(CHOH)_z$—$(CH_2)_{aa}$—$(CH2OH)_t$—R(64) or $(CH_2)_{ab}$—O—$(CH_2-CH_2O)_{ac}$—R(65),
R(64) and R(65) are hydrogen or methyl,
u=1, 2, 3 or 4,
v=zero, 1, 2, 3 or 4,
y, z and aa are identical or different and are zero, 1, 2, 3 or 4,
t=1, 2, 3 or 4,
R(51), R(53), R(54) and R(55) are identical or different and
are hydrogen or $(C_1-C_6)$-alkyl, or R(52) and R(53), or R(54) and R(55), respectively, are, together with the carbon atom carrying them, a $(C_3-C_8)$-cycloalkyl;

R(63) is hydrogen, $(C_1-C_6)$-alkyl, $(C_3-C_8)$-cycloalkyl or —$C_eH_{2e}$—R(81), e is zero, 1, 2, 3 or 4, R(56), R(57) and R(81) are, independently,
phenyl
which is unsubstituted or is substituted by 1–3 substituents from the group consisting of F, Cl, $CF_3$, methyl, methoxy or NR(82)R(66) with R(82) and R(66) being H or $(C_1-C_4)$-alkyl, or R(56), R(57) and R(81) are, independently, $(C_1-C_9)$-heteroaryl
which is unsubstituted or is substituted as phenyl;

R(58), R(59), R(60), R(61) and R(62) are hydrogen or methyl, or

R(3) and R(8) are, independently of each other,
R(67)—NH—$SO_2$—,
R(67) is R(68)R(69)N—(C=Y')—,
Y' is oxygen, S or N—R(70),
R(68) and R(69) are identical or different and
are hydrogen, $(C_1-C_8)$-alkyl, $(C_3-C_6)$-alkenyl or —$C_fH_{2f}$—R(71),
f is zero, 1, 2, 3 or 4,
R(71) is $(C_5-C_7)$-cycloalkyl or phenyl
which is unsubstituted or substituted by 1–3 substituents from the group consisting of F, Cl, $CF_3$, methoxy or $(C_1-C_4)$-alkyl, or
R(68) and R(69) together form 4 or 5 methylene groups of which one $CH_2$ group can be replaced by oxygen, S, NH, N—$CH_3$ or N-benzyl, where R(70) is defined as R(68) or is amidine;

and also the pharmaceutically tolerated salts thereof, where, however, compounds are excepted in which the radicals R(1) to R(10) are combined as follows:

| R(1) | R(2) | R(3) | R(4) | R(5) | R(6) | R(7) | R(8) | R(9) | R(10) |
|------|------|------|------|------|------|------|------|------|-------|
| H | Cl | Cl | H | H | H | H | Cl | Cl | H |
| H | H | $NH_2$ | H | H | H | H | $NH_2$ | H | H |
| H | H | H | H | H | H | H | H | H | H |
| Cl | H | H | H | H | H | H | H | H | Cl |
| H | H | Cl | H | H | H | H | Cl | H | H |
| H | H | $CH_3$ | H | H | H | H | $CH_3$ | H | H |
| H | H | $NH_2$ | H | H | H | H | H | H | H |
| H | H | Cl | H | H | H | H | H | H | H |
| H | H | $CH_3$ | H | H | H | H | H | H | H |

Compounds of the formula Ia are likewise particularly preferred in which:

R(5)=R(6)=hydrogen, the remaining residues are defined as above, and

R(1)=R(10)
R(2)=R(9)
R(3)=R(8)
R(4)=R(7)

Compounds of the formula Ia are likewise very particularly preferred in which:

R(1)=R(10)
=hydrogen, F, Cl, $CH_3$, OH, $NH_2$ and $CF_3$,

R(2)=R(9)
=hydrogen, F, Cl, Br, —C≡N, —$C_qF_{2q}CF_3$, R(13)—$SO_2$,
R(14)R(15)N—CO—, R(16)—CO— or R(17)R(18)N—$SO_2$—, R(13), R(14), R(16) and R(17) are, independently, $(C_1-C_8)$-alkyl, $(C_3-C_4)$-alkenyl, —$C_nH_{2n}$—R(20) or $CF_3$, n is zero or 1, q is zero, 1, 2, 3, 4 or 5, R(20) is $(C_3-C_6)$-cycloalkyl or phenyl
which is not substituted or is substituted by 1–2 substituents from the group consisting of F, Cl, $CF_3$, methyl, methoxy or NR(21)R(22),
R(21) and R(22) being hydrogen or methyl, where R(14), R(16) and R(17) also have the meaning of hydrogen, R(15) and R(18) are, independently, hydrogen or methyl, R(3) and R(8) are, independently of each other,

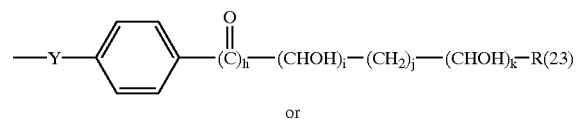

or

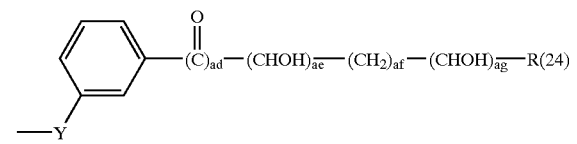

or

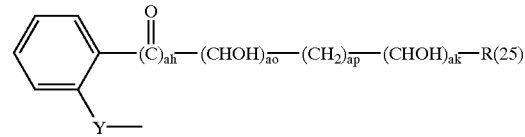

Y is oxygen, S or —NR(83),

R(23), R(24), R(25) and R(83) are, independently, hydrogen or methyl, h, ad and ah are, independently,
zero or 1, i, k, ae, ag, ao and ak are, independently,
zero, 1, 2 or 3, j, af and ap are, independently,
zero or 1, where, however, in each case, h, i and k are not simultaneously zero, ad, ae and ag are not simultaneously zero and ah, ao and ak are not simultaneously zero, or R(3)=R(8)
=hydrogen, F, Cl, Br, CN, $(C_1-C_8)$-alkyl, $CF_3$, $(C_3-C_8)$-alkenyl or —$C_gH_{2g}R(26)$ g is zero, 1 or 2, R(26) is $(C_3-C_6)$-cycloalkyl or phenyl
which is not substituted or is substituted by 1–2 substituents from the group consisting of F, Cl, $CF_3$, methyl, methoxy or NR(27)R(28), with R(27) and R(28) being H or $CH_3$;

or

R(3)=R(8)
=$(C_1-C_9)$-heteroaryl,
which is linked via C or N and which is unsubstituted or is substituted by 1–2 substituents from the group consisting of F, Cl, $CF_3$, $CH_3$, methoxy, hydroxyl, amino, methylamino or dimethylamino;

or

R(3) and R(8) are, independently of each other,

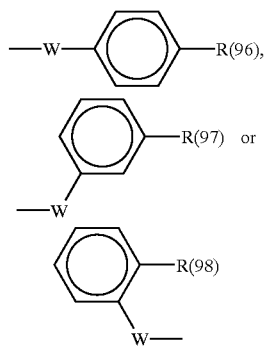

R(96), R(97) and R(98) are, independently, pyrrolyl, imidazolyl, pyrazolyl or pyridyl
which in each case is unsubstituted or substituted by 1 to 2 radicals from the group consisting of
F, Cl, $CF_3$, $CH_3$, methoxy, dimethylamino or benzyl,
W is oxygen, —S— or NR(99)—,
R(99) being hydrogen or methyl, or R(3)=R(8)
=—SR(29), —OR(30), —NR(31)R(32) or —CR(33)R(34)R(35),
R(29), R(30), R(31) and R(33) are, independently of each other,
—$C_aH_{2a}$—($C_1$–$C_9$)-heteroaryl
which is unsubstituted or is substituted by 1–2 substituents from the group consisting of F, Cl, $CF_3$, $CH_3$, methoxy, hydroxyl, amino, methylamino or dimethylamino,
a is zero or 1,
R(32), R(34) and R(35) are, independently of each other,
hydrogen or $CH_3$;

or

R(3)=R(8)
=R(72)—$SO_2$ or R(73)R(74)N—$SO_2$—,
R(72) is ($C_1$–$C_4$)-alkyl, $CF_3$, ($C_3$–$C_4$)-alkenyl or —$C_sH_{2s}$—R(75),
s is zero or 1,
R(75) is ($C_3$–$C_6$)-cycloalkyl or phenyl
which is not substituted or is substituted by 1–2 substituents from the group consisting of F, Cl, $CF_3$, methyl, methoxy or NR(76)R(77); with R(76) and R(77) being hydrogen or $CH_3$,
R(73) is hydrogen, ($C_1$–$C_4$)-alkyl, $CF_3$, ($C_3$–$C_4$)-alkenyl or
—$C_wH_{2w}$—R (78),
w is zero or 1,
R(78) is ($C_3$–$C_6$)-cycloalkyl or phenyl
which is not substituted or is substituted by 1–2 substituents from the group consisting of F, Cl, $CF_3$, methyl, methoxy or NR(79)R(80), with R(79) and R(80) being hydrogen or $CH_3$,
R(74) is hydrogen or $CH_3$,
where R(73) and R(74) can together be 4 or 5 methylene groups of which one $CH_2$ group can be replaced by oxygen, S, NH, N—$CH_3$ or N-benzyl;

or

R(3)=R(8)
=R(39)X—,
X is oxygen, S, NR(40), (C=O)A—, NR(41)C=MN$^{(*)}$R—(42)—,
M is oxygen, and
A is oxygen or NR(43),
R(39) is ($C_1$–$C_6$)-alkyl, ($C_3$–$C_4$)-alkenyl, $(CH_2)_bC_dF_{2d+1}$ or —$C_xH_{2x}$—R(44),
b is zero or 1,
d is 1–7,
x is zero or 1,
R(44) is ($C_3$–$C_6$)-cycloalkyl or phenyl
which is not substituted or is substituted by 1–2 substituents from the group consisting of F, Cl, $CF_3$, methyl, methoxy or NR(45)R(46), with R(45) and (46) being hydrogen or $CH_3$,
R(41) is hydrogen or ($C_1$–$C_4$)-alkyl,
R(42) is defined as R(39), where
R(39) and R(40), or R(39) and R(41), respectively, can together be 4 or 5 methylene groups of which one $CH_2$ group can be replaced by oxygen, S, NH, N—$CH_3$ or N-benzyl,
where A and $N^{(*)}$ are bonded to the phenyl nucleus of the benzoylguanidine parent substance;

or

R(3) and R(8) are
—SR (47), —OR(48), —NHR(49), —NR(50)R(51), —CHR(52)R(53),

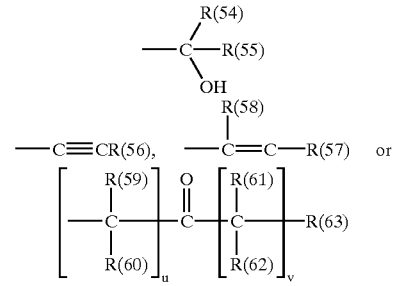

R(47), R(48), R(49), R(50) and R(52) are identical or different and are
—$(CH_2)_y$—$(CHOH)_z$—$(CH_2)_{aa}$—$(CH_2OH)_t$—R(64)
or
—$(CH_2)_{ab}$—O—$(CH_2$—$CH_2O)_{ac}$—R(65),
with R(64) and R(65) being hydrogen or methyl,
u is 1 or 2,
v is zero, 1 or 2,
y, z, aa, ab and ac are identical or different and are zero, 1 or 2,
t is 1, 2 or 3,
R(51), R(53), R(54) and R(55) are identical or different and are
hydrogen or methyl, or
R(52) and R(53), or R(54) and R(55), respectively, are, together with the carbon atom carrying them, a ($C_3$–$C_6$)-cycloalkyl,
R(63) is hydrogen, ($C_1$–$C_4$)-alkyl, ($C_3$–$C_6$)-cyclo-alkyl or —$C_eH_{2e}$—R(81),
e is zero, 1 or 2,
R(56), R(57) and R(81) are, independently of each other,
phenyl
which is unsubstituted or is substituted by 1–2 substituents from the group consisting of F, Cl, $CF_3$, methyl, methoxy or NR(65)R(66) with R(65) and R(66) being hydrogen or CH$_3$; or R(56), R(57) and R(81) are, independently of each other, (C$_1$–C$_9$)-heteroaryl
which is unsubstituted or is substituted as phenyl;

R(58), R(59), R(60), R(61) and R(62) are hydrogen or methyl, or

R(3) and R(8) are

R (67)—NH—SO$_2$—,

R(67) is R(68)R(69)N—(C=Y')—,

Y' is oxygen, S or N—R(70),

R(68) and R(69) are identical or different and are hydrogen, (C$_1$–C$_4$)-alkyl, (C$_3$–C$_4$)-alkenyl or —C$_f$H$_{2f}$—R(71), f is zero or 1, R(71) is (C$_5$–C$_7$)-cycloalkyl or phenyl
which is unsubstituted or is substituted by 1–2 substituents from the group consisting of F, Cl, CF$_3$, methoxy or methyl, or R(68) and R(69) together form 4 or 5 methylene groups of which one CH$_2$ group can be replaced by oxygen, S, NH, N—CH$_3$ or N-benzyl, R(70) is defined as R(68);

R(4)=R(7)

=(C$_1$–C$_8$)-alkyl, —C$_{al}$H$_{2al}$R(84) or CF$_3$, al is zero or 1,

R(84) is (C$_3$–C$_6$)-cycloalkyl or phenyl
which is not substituted or is substituted by 1–2 substituents from the group consisting of F, Cl, CF$_3$, methyl, methoxy or NR(85)R(86), with R(85) and R(86) being hydrogen or CH$_3$, or

R(4)=R(7)

=quinolyl, isoquinolyl, pyrrolyl, pyridyl or imidazolyl which are linked via C or N and which are unsubstituted or are substituted by 1–2 substituents from the group consisting of F, Cl, CF$_3$, CH$_3$, methoxy, hydroxyl, amino, methylamino or dimethylamino, or

R(4)=R(7)

=R(87)—SO$_{am}$ or R(88)R(89)N—SO$_2$—, am is 2,

R(87) is (C$_1$–C$_4$)-alkyl or CF$_3$.

R(88) is hydrogen, (C$_1$–C$_4$)-alkyl, CF$_3$ or —C$_{an}$H$_{2an}$—R(90), an is zero or 1, R(90) is phenyl
which is not substituted or is substituted by 1–2 substituents from the group consisting of F, Cl, CF$_3$, methyl, methoxy or NR(90)R(91), with R(90) and R(91) being hydrogen or CH$_3$, R(89) is hydrogen or CH$_3$, or

R(4)=R(7)

=—C=CR(93),

R(93) is phenyl
which is unsubstituted or is substituted by 1–2 substituents from the group consisting of F, Cl, CF$_3$, methyl, methoxy or NR(94)R(95) with R(94) and R(95) being hydrogen or CH$_3$;

R(5)=R(6)

=hydrogen, and also the pharmaceutically acceptable salts thereof.

(C$_1$–C$_9$)-Heteroaryl is, in particular, understood to mean radicals which are derived from phenyl or naphthyl and in which one or more CH groups are replaced by N, and/or in which at least two adjacent CH groups are replaced by S, NH or O (with the formation of a five-membered aromatic ring). In addition, one or both atoms of the condensation site of bicyclic radicals can also be N atoms (as in indolizinyl).

Heteroaryl is considered, in particular, to be furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl and cinnolinyl.

Should one of the substituents R(1) to R(198) contain one or more centers of asymmetry, these centers can then be in either the S or the R configuration. The compounds can be present as optical isomers, as diastereomers, as racemates, or as mixtures thereof.

The designated alkyl and perfluoroalkyl radicals can be present either in the straight-chain or the branched form.

The invention relates furthermore to a process for preparing the compounds I, wherein either two equivalents of the compounds of the formula II are reacted with one equivalent of guanidine

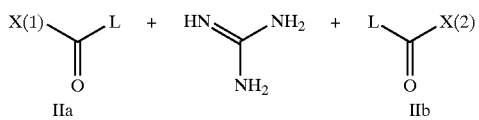

where X(1) and X(2) have the given meaning and L is a leaving group which can readily be substituted nucleophilically, or a compound of the formula IIa

is reacted with a compound of the formula III

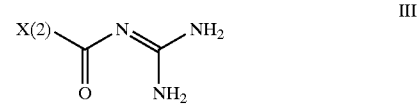

with the participation of a base, for example K$_2$CO$_3$, NaOH or triethylamine, where X(1) and X(2) have the given meaning and L is a leaving group which can readily be substituted nucleophilically.

The activated acid derivatives of the formula II, in which L is an alkoxy, preferably a methoxy, group, a phenoxy group, a phenylthio, methylthio or 2-pyridylthio group, or a nitrogen heterocycle, preferably 1-imidazolyl, are advantageously obtained, in a manner known per se, from the underlying carbonyl chlorides (formula II, L=Cl), which, for their part, can be prepared, once again in a manner known per se, from the underlying carboxylic acids (formula II, L=OH), for example using thionyl chloride.

In addition to the carbonyl chlorides of the formula II (L=Cl), other activated acid derivatives of the formula II can also be prepared, in a manner known per se, directly from the underlying benzoic acid derivatives (formula II, L=OH)

as can, for example, the methyl esters of the formula II with L=OCH$_3$ by treatment with gaseous HCl in methanol, the imidazolides of the formula II by treatment with carbonyldiimidazole [L=1-imidazolyl, Staab, Angew. Chem. Int. Ed. Engl. 1, 351–367 (1962)], the mixed anhydrides II with Cl —COOC$_2$H$_5$ or tosyl chloride in the presence of triethylamine in an inert solvent, in addition to which there is also the activation of benzoic acids with dicyclohexylcarbodiimide (DCC) or with O-[(cyano(ethoxycarbonyl)methylene)amino]-1,1,3,3-tetramethyluronium tetrafluoroborate ("TOTU") [Proceedings of the 21st European Peptide Symposium, Peptides 1990, Editors E. Giralt and D. Andreu, Escom, Leiden, 1991]. A series of suitable methods for preparing activated carboxylic acid derivatives of the formula II is given, with citation of the source literature, on p. 350 in J. March, Advanced Organic Chemistry, Third Edition (John Wiley & Sons, 1985).

An activated carboxylic acid derivative of the formula II is reacted with guanidine, in a manner known per se, in a protic or aprotic polar, but nevertheless inert, organic solvent. In this context, methanol, isopropanol or THF, at a temperature of from 20° C. up to the boiling temperature of these solvents, have proved of value when reacting the methylbenzoates (II, L=OMe) with guanidine. Most of the reactions of compounds II with salt-free guanidine were advantageously carried out in aprotic inert solvents such as THF, dimethoxyethane or dioxane. However, water can also be used, while employing a base such as, for example, NaOH, as the solvent, when reacting II with guanidine.

When L denotes Cl, the reaction is advantageously carried out with the addition of an acid-capturing agent, for example in the form of excess guanidine, for binding and thus removing the hydrohalic acid.

Some of the underlying benzoic acid derivatives of the formula II are known and are described in the literature. The unknown compounds of the formula II may be prepared by methods which are known from the literature. The introduction of some of the substituents is achieved by the methods, which are known from the literature, of palladium-mediated cross-coupling of aryl halides or aryl triflates with, for example, organostannanes, organoboronic acids, organoboranes, or organocopper or organozinc compounds, or terminal alkynes. The resulting benzoic acids are converted into activated benzoic acid derivatives of the formula II by one of the above-described process variants. The compounds of the formula II are either converted directly into the compounds of the formula I according to the invention or transformed initially with guanidine into compounds of the formula III which, following isolation, are converted into the compounds of the formula I according to the invention by reaction with a further compound of the formula II.

In general, dialkanoyl-substituted guanidines of the formula I are weak bases and can bind acid with the formation of salts. Suitable acid addition salts are the salts of all pharmacologically tolerated acids, for example halides, in particular hydrochlorides, lactates, sulfates, citrates, tartrates, acetates, phosphates, methylsulfonates and p-toluenesulfonates.

The compounds I are dialkanoyl-substituted guanidines which both directly inhibit the cellular sodium/proton exchanger (Na$^+$/H$^+$ exchanger or Na$^+$/H$^+$ antiporter) and also lose one of their acyl radicals in vivo, with a half life of between 1 minute and 10 hours, and thus, in turn, liberate monoacylguanidines, which are efficient inhibitors of the cellular sodium/proton exchanger. Compounds of the formula I are therefore potent inhibitors of the cellular sodium/ proton exchanger and lead to an improvement in the kinetics of the underlying monoacylguanidines. Over and above this, they give rise, owing to their lipophilic nature, to higher concentrations in the CNS of active compounds in the form of dialkanoylguanidines and monoacylguanidines than are achieved using the monoacylguanidines.

As a consequence of their pharmacological properties, the compounds are outstandingly suitable for use as antiarrhythmic pharmaceuticals possessing a cardioprotective component for the prophylaxis and treatment of infarction and for the treatment of angina pectoris, in connection with which they also inhibit or strongly reduce, in a preventive manner, the pathophysiological processes associated with the genesis of is chemically induced damage, in particular associated with the elicitation of is chemically induced cardiac arrhythmias. On account of their protective effects against pathological hypoxic and ischemic situations, the compounds of the formula I according to the invention can, as a consequence of inhibiting the cellular Na$^+$/H$^+$ exchange mechanism, be used as pharmaceuticals for treating all acute or chronic damage elicited by ischemia, or diseases induced primarily or secondarily thereby. This is the case with regard to their use as pharmaceuticals for surgical interventions, for example in organ transplantations, where the compounds can be used both for protecting the organs in the donor prior to and during removal, for protecting organs which have been removed, for example when they are being treated with or stored in physiological bathing fluids, and when transferring the organs into the recipient. The compounds are likewise valuable protective pharmaceuticals to be used when carrying out angioplastic surgical interventions, for example on the heart or on peripheral vessels. In conformity with their ability to protect against ischemically induced damage, the compounds are also suitable for use as pharmaceuticals for treating ischemias of the nervous system, in particular of the CNS, in connection with which they are suitable, for example, for treating stroke or cerebral edema. Over and above this, the compounds of the formula I according to the invention are also suitable for use in the treatment of forms of shock, such as, for example, allergic, cardiogenic, hypovolemic and bacterial shock.

In addition to this, the compounds of the formula I according to the invention are notable for their strong inhibitory effect on the proliferation of cells, for example the proliferation of fibroblast cells and the proliferation of the smooth muscle cells of the blood vessels. For this reason, the compounds of the formula I are valuable therapeutic agents for use in diseases in which cell proliferation represents a primary or secondary cause and may, therefore, be used as anti-atherosclerotic agents, and as agents against diabetic late complications, cancerous diseases, fibrotic diseases such as pulmonary fibrosis, hepatic fibrosis or renal fibrosis, and against organ hypertrophies or hyperplasias, in particular hyperplasia or hypertrophy of the prostate.

The compounds according to the invention are efficient inhibitors of the cellular sodium/proton antiporter (Na$^+$/H$^+$ exchanger), which, in numerous diseases (essential hypertension, atherosclerosis, diabetes, etc.), is also elevated in those cells which are readily accessible to measurement, such as, for example, erythrocytes, thrombocytes or leucocytes. The compounds according to the invention therefore represent outstanding and simple scientific tools, for example in their use as diagnostic aids for defining and differentiating particular forms of hypertension and also of atherosclerosis, diabetes, proliferative diseases, etc. In addition to this, the compounds of the formula I can suitably be used in preventive therapy for preventing the genesis of high blood pressure, for example of essential hypertension.

In this context, pharmaceuticals which contain a compound I may be administered orally, parenterally, intravenously or rectally, or by inhalation, the preferred route of administration depending on the given features of the disease. In this context, the compounds I may be used either alone or together with pharmaceutical auxiliary substances, both in veterinary and in human medicine.

Owing to his specialist knowledge, the person skilled in the art is familiar with those auxiliary substances which are suitable for the desired pharmaceutical formulation. Antioxidants, dispersants, emulsifiers, defoamers, taste corrigents, preservatives, solubilizers or dyes, for example, can be used in addition to solvents, gel formers, suppository bases, tablet auxiliaries and other active compound excipients.

For a form for oral use, the active compounds are mixed with the additives, such as carrier substances, stabilizers or inert diluents, which are suitable for the purpose, and brought by the customary methods into the forms, such as tablets, coated tablets, hard gelatin capsules, or aqueous, alcoholic or oily solutions, which are suitable for administration. Gum arabic, magnesium hydroxide, magnesium carbonate, potassium phosphate, lactose, glucose or starch, in particular corn starch, can, for example, be used as inert excipients. In this context, the preparation can be effected either as a dry granulate or as a wet granulate. Vegetable or animal oils, for example, such as sunflower oil or cod-liver oil, are suitable for use as oily excipients or as solvents.

For subcutaneous or intravenous administration, the active compounds are brought into solution, suspension or emulsion, if desired using the substances, such as solubilizers, emulsifiers or other auxiliary substances, which are customary for the purpose. Examples of suitable solvents are: water, physiological sodium chloride solution or alcohols, for example ethanol, propanol or glycerol, as well as sugar solutions, such as glucose or mannitol solutions, or else a mixture of the different solvents mentioned.

Solutions, suspensions or emulsions of the active compound of the formula I in a pharmaceutically harmless solvent, such as, in particular, ethanol or water, or in a mixture of such solvents, represent examples of suitable pharmaceutical formulations for administration in the form of aerosols or sprays.

As required, the formulation can also contain additional pharmaceutical auxiliary substances such as surfactants, emulsifiers and stabilizers, as well as a propellent gas. Such a preparation customarily contains the active compound in a concentration of from about 0.1 to 10, in particular of from about 0.3 to 3, % by weight.

The dosage of the active compound of the formula I to be administered, and the frequency of administration, depend on the strength and duration of the effect of the compounds used; additionally also on the nature and severity of the disease to be treated and on the sex, age, weight and individual responsiveness of the mammalian subject to be treated.

On average, the daily dose of a compound of the formula I is, for a patient of approximately 75 kg in weight, at least 0.001 mg/kg, preferably 0.01 mg/kg, up to at most 10 mg/kg, preferably 1 mg/kg, of body weight. In acute manifestations of the disease, for example immediately after suffering a cardiac infarction, even greater and, in particular, more frequent dosages may also be necessary, for example up to 4 individual doses per day. In the case of i.v. use in particular, for example in an infarction patient in intensive care, up to 200 mg per day may be necessary.

List of abbreviations:

| | |
|---|---|
| Bn | benzyl |
| $CH_2Cl_2$ | dichloromethane |
| DCI | desorption chemical ionization |
| DIP | diisopropyl ether |
| DME | dimethoxyethane |
| DMF | N,N-dimethylformamide |
| EA | ethyl acetate (EtOAc) |
| EI | electron impact |
| eq. | equivalent |
| ES | electrospray ionization |
| Et | ethyl |
| FAB | fast atom bombardment |
| HEP | n-heptane |
| Me | methyl |
| MeOH | methanol |
| mp | melting point |
| MTB | methyl tert-butyl ether |
| Pd/C | palladium on carbon |
| Pt/C | platinum on carbon |
| RT | room temperature |
| THF | tetrahydrofuran |
| CNS | central nervous system |

EXPERIMENTAL SECTION

General Instructions for Preparing Monoacylguanidines (III)

Variant A: from carboxylic acids (II, L=OH)

1.0 eq. of the carboxylic acid derivative of the formula II is dissolved or suspended in anhydrous THF (5 ml/mmol), and 1.1 eq. of carbonyldiimidazole are then added. After the mixture has been stirred at RT for 2 hours, 5.0 eq. of guanidine are introduced into the reaction solution. After the mixture has been stirred overnight, the THF is distilled off under reduced pressure in a rotary evaporator and water is added to the residue, which is adjusted to from pH 6 to 7 with 2N HCl; the corresponding monoacylguanidine (formula III) is then filtered off. The monoacylguanidines obtained in this way can be converted into the corresponding salts by treatment with aqueous, methanolic or ethereal hydrochloric acid or other pharmacologically tolerated acids.

General Instructions for Preparing Monoacylguanidines (III)

Variant B: from alkyl carboxylates (II, L=O-alkyl)

1.0 eq. of the alkyl carboxylate of the formula II and also 5.0 eq. of guanidine (free base) are dissolved in isopropanol or suspended in THF and boiled under reflux until the reaction is complete (monitoring by thin layer chromatography) (typical reaction time, from 2 to 5 h). The solvent is distilled off under reduced pressure in a rotary evaporator and the residue is taken up in EA and washed 3× with a solution of $NaHCO_3$. Drying takes place over $Na_2SO_4$, after which the solvent is distilled off in vacuo and the residue is chromatographed on silica gel using a suitable eluent, for example EA/MeOH 5:1.

(Salt formation, compare variant A)

General Instructions for Preparing Dialkanoylguanidines (I)

Variant F: from carboxylic acids (II, L=OH)

2.0 eq. of the carboxylic acid derivative of the formula II are dissolved or suspended in anhydrous THF (5 ml/mmol), and 2.2 eq. of carbonyldiimidazole are then added. After the mixture has been stirred at RT for 2 hours, 1.0 eq. of guanidine is introduced into the reaction solution. After the mixture has been stirred overnight, the THF is distilled off under reduced pressure in a rotary evaporator, and water is added to the residue, which is adjusted to from pH 6 to 7 with 2N HCl; the corresponding dialkanoylguanidine (formula I) is then filtered off. The monoacylguanidines obtained in this way can be converted into the corresponding salts by treatment with aqueous, methanolic or ethereal hydrochloric acid or other pharmacologically tolerated acids.

General Instructions for Preparing
Dialkanoylguanidines (I)
Variant G: from carboxylic acid esters (II, L=O-alkyl)

2.0 eq. of the alkyl carboxylate of the formula II and also 1.0 eq. of guanidine (free base) are dissolved in isopropanol or suspended in THF and boiled under reflux until the reaction is complete (monitoring by thin layer chromatography) (typical reaction time, from 2 to 5 h). The solvent is distilled off under reduced pressure in a rotary evaporator and the residue is taken up in EA and washed 3× with a solution of NaHCO$_3$. Drying takes place over Na$_2$SO$_4$, after which the solvent is distilled off in vacuo and the residue is chromatographed on silica gel using a suitable eluent, e.g. EA/MeOH 5:1.

(Salt formation, compare variant A)

General Instructions for Preparing
Dialkanoylguanidines (I)
Variant K: from monoacylguanidines (III) and a carboxylic acid derivative of the formula II (for example, a carboxylic acid ester or activated carboxylic acid)

1.0 eq. of the monoacylguanidine of the formula III (free base) and also 1.0 eq. of the carboxylic acid derivative of the formula II (for the preparation of an activated carboxylic acid, compare variant A) are dissolved or suspended, respectively, in isopropanol or in THF and the mixture is stirred at an appropriate temperature (RT to reflux) until the reaction is complete (monitoring by thin layer chromatography). The solvent is distilled off under reduced pressure in a rotary evaporator and the residue is taken up in EA and washed 3× with a solution of NaHCO$_3$. Drying over takes place Na$_2$SO$_4$, after which the solvent is distilled off in vacuo and the residue is chromatographed on silica gel using a suitable eluent, e.g. EA/MeOH 10:1.

(Salt formation, compare variant A)

EXAMPLE 1

Bis(3-methylsulfonyl-4-i-propylbenzoyl)guanidine
a) 3-Methylsulfonyl-4-i-propylbenzoyl Chloride 4.0 g of 3-methylsulfonyl-4-i-propylbenzoic acid, 1.5 ml of thionyl chloride and 3 drops of DMF are heated under reflux for 10 h in 30 ml of toluene. The solvent is subsequently removed in vacuo and the product is taken for further use without purification.

b) Bis(3-methylsulfonyl-4-i-propylbenzoyl)guanidine

The acid chloride 1 a) and 3.9 g of 3-methylsulfonyl-4-i-propylbenzoylguanidine are dissolved in 50 ml of DMF, and 3.4 g of K$_2$CO$_3$ are then added. The mixture is stirred at RT for 4 h and then left to stand overnight. The solution is subsequently concentrated and the residue stirred up in 200 ml of water. The solid is filtered off and washed with 100 ml of water. This solid is then dissolved in 100 ml of EA and washed 1× with 10 ml of 1N HCl and then 1× with 50 ml of NaCl solution. Drying takes place over Na$_2$SO$_4$ and the solvent is removed in vacuo. A yellow solid is obtained which is purified by being triturated twice with 20 ml of diethyl ether and subsequently being filtered off. The product is dried in vacuo and 1.9 g are obtained of a white solid, mp 218–221° C.

$R_f$ (CH$_2$Cl$_2$/MeOH 20:1)=0.57 MS (ES): 508 (M+1).

Precursors

4-Isopropyl-3-methylsulfonylbenzoylguanidine-methanesulfonate:

Colorless crystals, mp 226–28° C.

Synthesis route:

a) 4-Isopropylbenzoic acid, by the oxidation of 4-isopropylbenzaldehyde with sodium perborate in acetic acid at 50° C., mp 118° C., b) 4-isopropyl-3-chlorosulfonylbenzoic acid, from a) by heating in chlorosulfuric acid at 95° C. for 3 h, mp 203–4° C., c) 2-isopropyl-5-carboxybenzenesulfinic acid, from b) by reduction with sodium sulfite at 60° C. in aqueous sodium hydroxide solution (pH≈9–10), mp 205–7° C., d) 4-isopropyl-3-methylsulfonylbenzoic acid, from c) by alkylation with methyl bromide in the presence of NaOH in DMF at 60° C. for 3 h, mp 209–11° C., e) 4-isopropyl-3-methylsulfonylbenzoylguanidine-methane-sulfonate, from d) by reaction with thionyl chloride in toluene (reflux) for 1 h. After the toluene has been stripped off, the residue is taken up in THF and the resulting acid chloride is added to a mixture of guanidine hydrochloride, 2N NaOH and THF. After the mixture has been stirred at 30–40° C. for 4 h, the THF is distilled off, whereupon the product accrues in crystalline form as a free base. Subsequent treatment with methanesulfonic acid yields the salt.

EXAMPLE 2

Bis(4-fluoro-3-trifluoromethylbenzoyl)guanidine
a) 4-Fluoro-3-trifluoromethylbenzoyl Chloride 1.5 g of 4-fluoro-3-trifluoromethylbenzoic acid, 0.65 ml of thionyl chloride and two drops of DMF are heated under reflux for 12 h in 17 ml of toluene and the mixture is subsequently concentrated and used without further purification.

b) Bis(4-fluoro-3-trifluoromethylbenzoyl)guanidine

The acid chloride 2a) and 0.87 g of 4-fluoro-3-trifluoromethylbenzoylguanidine are dissolved in 15 ml of DMF, and 1.3 g of potassium carbonate are then added. The mixture is stirred at RT for 20 h and then worked up as described under 1b). The resulting, clear oil is purified by column chromatography (silica gel, heptane/EA 8:2), and a colorless solid, mp 143–45° C., is obtained.

$R_f$ (heptane/EA 7:3)=0.7; MS (ES): 440 (M+1).

Precursor

4-Fluoro-3-trifluoromethylbenzoylguanidine:

Colorless crystals, mp 159–60° C.

Synthesis route:

4-Fluoro-3-trifluoromethylbenzoylguanidine, from 4-fluoro-3-trifluoromethylbenzoic acid by reaction with N,N'-carbonyldiimidazole in THF at RT and subsequent addition of guanidine.

EXAMPLE 3

Bis[4-(1-imidazolyl)-3-trifluoromethylbenzoyl] guanidine and

EXAMPLE 4

N-[4-(1-Imidazolyl)-3-trifluoromethylbenzoyl]-N'-(4-fluoro-3-trifluoromethylbenzoyl)guanidine Hydrochloride 0.25 g of bis(4-fluoro-3-trifluoromethylbenzoyl) guanidine, 0.16 g of imidazole and 0.16 g of potassium carbonate are heated for 16 h in 5 ml of DMF, and after that the solvent is evaporated. Separation of the crude product by column chromatography yielded 0.12 g of bis[4-(1-imidazolyl)-3-trifluoromethylbenzoyl]guanidine as a colorless solid, mp 130° C., decomp., $R_f$ ($CH_{2Cl2}$/MeOH 9:1)=0.4 MS (ES): 536 (M+1) and 0.07 g of N-[4-(1-imidazolyl)-3-trifluoromethylbenzoyl]-N'-(4-fluoro-3-trifluoromethylbenzoyl)guanidine as an oil. Treatment with $HCl_g$/ether yielded 0.06 g of N-[4-(1-imidazolyl)-3-trifluoromethylbenzoyl]-N'-(4-fluoro-3-trifluoromethylbenzoyl)guanidine hydrochloride as a colorless solid, mp 217–218, decomp., $R_f$ ($CH_2Cl_2$/MeOH 9:1)= 0.53; MS (ES): 488 (M+1)

EXAMPLE 5

N,N'-Bis(1,2,3,4-tetrahydronaphthalene-2-carbonyl)guanidide was prepared according to variant F from 1,2,3,4-tetrahydronaphthalene-2-carboxylic acid and isolated as a free base.

MS (ES): 376 (M+1); mp 99° C.

Was also prepared in accordance with variant K via 1,2,3,4-tetrahydronaphthalene-2-carbonylguanidine [prepared in accordance with variant A from 1,2,3,4-tetrahydronaphthalene-2-carboxylic acid: MS (ES): 218 (M+1)] and 1,2,3,4-tetrahydronaphthalene-2-carboxylic acid.

EXAMPLE 6

N,N'-Bis[(E)-2-methylcinnamoyl]guanidide was prepared from (E)-2-methylcinnamic acid in accordance with variant F and isolated as the hydrochloride.

MS (ES): 348 (M+1); mp 193° C.

EXAMPLE 7

N,N'-Bis[3-(2-trifluoromethylphenyl)propionyl]guanidide was prepared from 3-(2-trifluoromethylphenyl)propionic acid in accordance with variant F and isolated as the hydrochloride.

MS (ES): 460 (M+1); mp 75° C.

EXAMPLE 8

N,N'-Bis[3-(2,5-difluorophenyl)-2-methylpropionyl]guanidide

Was prepared from 3-(2,5-difluorophenyl)-2-methylpropionic acid in accordance with variant F and isolated as the hydrochloride.

MS (ES): 424 (M+1); mp amorphous.

PHARMACOLOGICAL DATA

Inhibition of the $Na^+/H^+$ Exchanger of Rabbit Erythrocytes

New Zealand White rabbits (Ivanovas) were given a standard diet containing 2% cholesterol for six weeks in order to activate $Na^+/H^+$ exchange and thus to be able to use flame photometry to determine the $Na^+$ influx into the erythrocytes via $Na^+/H^+$ exchange. The blood was removed from the aural arteries and rendered incoagulable by the addition of 25 IU of potassium heparin per ml. One part of each sample was used for the duplicate determination of the hematocrit by centrifugation. Aliquots of in each case 100 µl were employed for measuring the initial content of $Na^+$ in the erythrocytes.

In order to determine the amiloride-sensitive sodium influx, 100 µl of each blood sample were in each case incubated, at pH 7.4 and 37° C., in 5 ml of a hyperosmolar salt/sucrose medium (mmol/l: 140 NaCl, 3 KCl, 150 sucrose, 0.1 ouabain, 20 tris(hydroxymethyl)aminomethane). The erythrocytes were then washed three times with ice cold $MgCl_2$/ouabain solution (mmol/l: 112 $MgCl_2$, 0.1 ouabain) and hemolyzed in 2.0 ml of distilled water. The intracellular content of sodium was determined by flame photometry.

The nett influx of $Na^+$ was calculated from the difference between the initial sodium values and the sodium content of the erythrocytes following incubation. The amiloride-inhibitable sodium influx was given by the difference in the sodium content of the erythrocytes following incubation with and without $3 \times 10^{-4}$ mol/l amiloride. The same procedure was also used in the case of the compounds according invention.

Results relating to the inhibition of the $Na^+/H^+$ exchanger:

| $IC_{50}$ (µmol) | Example |
|---|---|
| 10 | 1 |
| 10 | 2 |
| 5 | 3 |
| 3 | 4 |
| 0.3 | 5 |
| 1.1 | 6 |
| 2 | 7 |
| 0.3 | 8 |

The following were obtained in analogy with Example 1:

| Example | R(1) = R(10) | R(2) = R(9) | R(3) = R(8) | R(4) = R(7) | R(5) = R(6) |
|---|---|---|---|---|---|
| 9 | H | H | Cl | n-BuNH— | H |
| 10 | H | H | 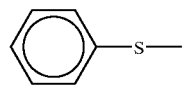 | $H_2NSO_2$— | H |
| 11 | H | H | 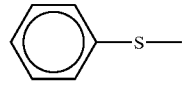 | $MeSO_2$ | H |

-continued

| Example | R(1) = R(10) | R(2) = R(9) | R(3) = R(8) | R(4) = R(7) | R(5) = R(6) |
|---|---|---|---|---|---|
| 12 | H | pyrrolidin-1-yl | Me | H | H |
| 13 | H | pyrrolidin-1-yl | C₆H₄-O-(methoxyphenyl) | H | H |
| 14 | H | piperidin-1-yl | Me | H | H |
| 15 | H | piperidin-1-yl | Cl | H | H |
| 16 | H | pyrrolidin-1-yl | MeSO₂ | H | H |
| 17 | H | H | NH₂ | MeSO₂ | H |
| 18 | H | H | cyclopentyl-NH— | MeSO₂ | H |
| 19 | H | H | methoxyphenyl-O— | MeSO₂ | H |
| 20 | H | H | 2-Cl-C₆H₄-S— | MeSO₂ | H |
| 21 | H | H | 4-Me-C₆H₄-NH— | MeSO₂— | H |
| 22 | H | H | 3-Me-C₆H₄-NH— | MeSO₂— | H |
| 23 | H | H | 2,4-diMe-C₆H₃-NH— | MeSO₂— | H |
| 24 | H | H | piperidin-1-yl | Cl₂— | H |
| 25 | H | H | (CH₃)₂CHCH₂—O— | MeSO₂— | H |
| 26 | H | H | 2-OMe-C₆H₄-S— | MeSO₂— | H |

-continued

| Example | R(1) = R(10) | R(2) = R(9) | R(3) = R(8) | R(4) = R(7) | R(5) = R(6) |
|---|---|---|---|---|---|
| 27 | H | H | 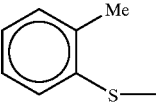 2-Me, 1-SMe phenyl | MeSO$_2$— | H |
| 28 | H | H | 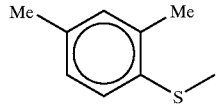 2,4-diMe, 1-SMe phenyl | MeSO$_2$ | H |
| 29 | H | 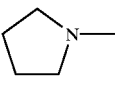 pyrrolidinyl | 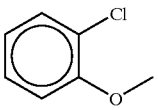 2-Cl, 1-OMe phenyl | H | H |
| 30 | H | 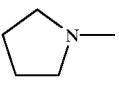 pyrrolidinyl | 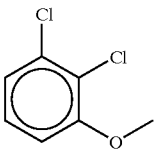 2,3-diCl, 1-OMe phenyl | H | H |
| 31 | H | 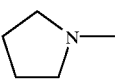 pyrrolidinyl | 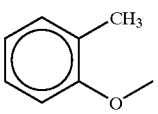 2-CH$_3$, 1-OMe phenyl | H | H |
| 32 | H | 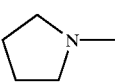 pyrrolidinyl | 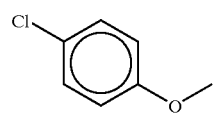 3-Cl, 1-OMe phenyl | H | H |
| 33 | H | 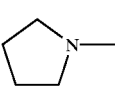 pyrrolidinyl | 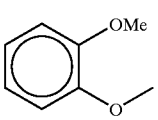 1,2-diOMe phenyl | H | H |
| 34 | H | 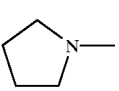 pyrrolidinyl | 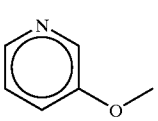 methoxypyridyl | H | H |
| 35 | H | H | 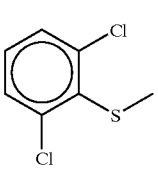 2,6-diCl, 1-SMe phenyl | MeSO$_2$— | H |
| 36 | H | H | 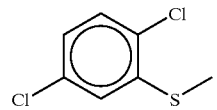 2,5-diCl, 1-SMe phenyl | MeSO$_2$— | H |
| 37 | Me | H | H | Me | H |
| 38 | H | Me | Me | H$_2$NSO$_2$— | H |
| 39 | H | H | H | CF$_3$ | H |
| 40 | H | 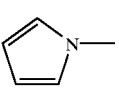 pyrrolyl | Cl | H | H |
| 41 | H | H | MeNH— | MeSO$_2$— | H |
| 42 | H | H | Et$_2$N— | MeSO$_2$— | H |

-continued
| Example | R(1) = R(10) | R(2) = R(9) | R(3) = R(8) | R(4) = R(7) | R(5) = R(6) |
|---|---|---|---|---|---|
| 43 | H | t-Bu | OH | t-Bu | H |
| 44 | H | H | 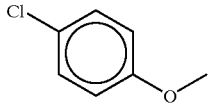 | MeSO$_2$— | H |
| 45 | H | H | 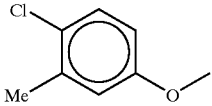 | MeSO$_2$— | H |
| 46 | H | H | 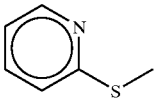 | MeSO$_2$— | H |
| 47 | H | H | 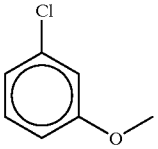 | MeSO$_2$— | H |
| 48 | H | H | 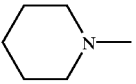 | MeSO$_2$— | H |
| 49 | H | H | 2-naphthyl | MeSO$_2$— | H |
| 50 | H | H | 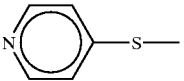 | MeSO$_2$— | H |
| 51 | H | 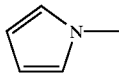 | Me | H | H |
| 52 | H | 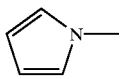 | 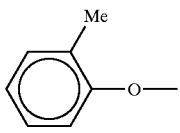 | H | H |
| 53 | H | Cl | Et$_2$N— | MeSO$_2$— | H |
| 54 | H | Me$_2$N— | H | CF$_3$ | H |
| 55 | H | H | 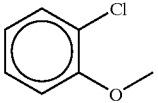 | MeSO$_2$— | H |
| 56 | H | Br | NH$_2$ | Br | H |
| 57 | H | Cl | H | CF$_3$ | H |
| 58 | H | H | 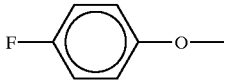 | MeSO$_2$— | H |
| 59 | H | H | 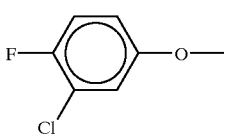 | MeSO$_2$— | H |

-continued

| Example | R(1) = R(10) | R(2) = R(9) | R(3) = R(8) | R(4) = R(7) | R(5) = R(6) |
|---|---|---|---|---|---|
| 60 | H | CF$_3$ | H | CF$_3$ | H |
| 61 | H | H | Me | Me | H |
| 62 | H | I | H | CF$_3$ | H |
| 63 | H | Me | H | Me | H |
| 64 | H | H | t-Bu | H | H |
| 65 | H | H | 4-F-C$_6$H$_4$-NH- | MeSO$_2$— | H |
| 66 | H | H | Cl | Me | H |
| 67 | H | H | Me | Br | H |
| 68 | H | H | MeO— | Cl | H |
| 69 | H | Cl | MeO— | Cl | H |
| 70 | H | Br | H | Br | H |
| 71 | H | H | PhCH$_2$CH$_2$— | MeSO$_2$— | H |
| 72 | H | H | PhC≡C— | MeSO$_2$— | H |
| 73 | NH$_2$ | Br | H | Me | H |
| 74 | H | N$_3$ | H | CF$_3$ | H |
| 75 | H | H | t-Bu | Me$_2$N— | H |
| 76 | H | H | 4-MeO-3-HO-C$_6$H$_3$— | MeSO$_2$— | H |
| 77 | H | 1-pyrrolyl | H | H | H |
| 78 | H | 1-pyrrolyl | MeO— | H | H |
| 79 | H | H | Br | Me | H |
| 80 | H | H | F | Cl | H |
| 81 | H | t-Bu | H | t-Bu | H |
| 82 | NH$_2$ | H | H | Cl | H |
| 83 | H | 1-pyrrolyl | H | Me$_2$N | H |
| 84 | H | Me$_2$N | H | Cl | H |
| 85 | H | H | 7-iso-quinolinoxy | MeSO$_2$— | H |
| 86 | H | H | 6-quinolinoxy | MeSO$_2$— | H |
| 87 | H | H | 4-MeO-C$_6$H$_4$-C(O)CH$_3$ | MeSO$_2$— | H |
| 88 | H | H | 4-MeO-C$_6$H$_4$-CH(OH)CH$_3$ | MeSO$_2$— | H |

-continued

| Example | R(1) = R(10) | R(2) = R(9) | R(3) = R(8) | R(4) = R(7) | R(5) = R(6) |
|---|---|---|---|---|---|
| 89 | H | H | (CH₃)₂CH—CH₂— | MeSO₂— | H |
| 90 | H | H | cyclopentylmethyl | MeSO₂— | H |
| 91 | H | H | 4-methoxyphenyl | Me₂N— | H |
| 92 | H | H | 4-chloro-3-methoxyphenyl | Me₂N— | H |
| 93 | H | Me | Me₂N— | Me | H |
| 94 | H | H | 4-methoxyphenyl | 1-pyrrolyl | H |
| 95 | H | Me | 1-methylpyrrol-2-yl | Me | H |
| 96 | H | H | ClCH=C(CH₃) | MeSO₂ | H |
| 97 | H | H | i-Pr | Cl | H |
| 98 | H | H | i-Pr | 1-pyrrolyl | H |
| 99 | H | H | 5-quinolinoxy | MeSO₂— | H |
| 100 | H | cyclopentylmethyl | H | CF₃ | H |
| 101 | H | i-Pr | H | MeSO₂— | H |
| 102 | H | i-Pr | H | CF₃ | H |
| 103 | H | H | i-Pr | H | H |
| 104 | NH₂ | H | Br | Br | H |
| 105 | H | H | 1-(4-methoxyphenyl)-1,2-dihydroxypropyl | MeSO₂— | H |
| 106 | H | 1-methylpyrrol-2-yl | H | MeSO₂— | H |
| 107 | H | H | 2-(4-methoxyphenyl)-1-benzylimidazol-... | MeSO₂— | H |
| 108 | H | Cl | N-phenyl-N'-methylureido | Cl | H |
| 109 | H | Me₂N | i-Pr | MeSO₂— | H |

-continued

| Example | R(1) = R(10) | R(2) = R(9) | R(3) = R(8) | R(4) = R(7) | R(5) = R(6) |
|---|---|---|---|---|---|
| 110 | H | MeHN— | i-Pr | MeSO₂— | H |
| 111 | H | Cl | Cl | Cl | H |
| 112 | H | Cl | H₂N— | Me | H |
| 113 | H | Cl | H₂N | Cl | H |
| 114 | H | H | 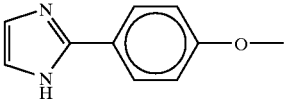 | MeSO₂— | H |
| 115 | H | H | 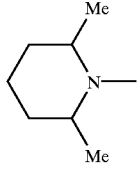 | MeSO₂— | H |
| 116 | H | H | i-Pr | Me₂N— | H |
| 117 | CF₃ | H | H | CF₃ | H |
| 118 | H | Br | H | Me | H |
| 119 | H | Me | Cl | Me | H |
| 120 | H | Me₂N | Me | Br | H |
| 121 | H | CF₃ | H | MeHN— | H |
| 122 | H | H | (CH₃)₂CH—CH₂ | CH₃CO— | H |
| 123 | H | H | 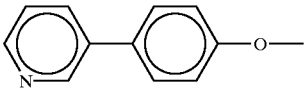 | MeSO₂— | H |
| 124 | H | H | H | CF₃—O— | H |
| 125 | H | Cl | Me₂N | Me | H |
| 126 | H | H |  | Cl | H |
| 127 | H | Cl | Me₂N- | Cl | H |
| 128 | H | H | 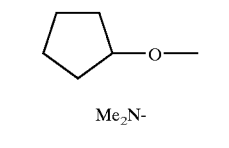 | MeSO₂— | H |
| 129 | H | H | i-Pr | CH₃CO— | H |
| 130 | H | Br | BnO— | CH₃CO— | H |
| 131 | H | H | Br | CF₃ | H |
| 132 | H | H | MeO— | i-Pr | H |
| 133 | H | H | 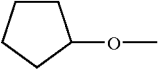 | MeSO₂— | H |
| 134 | H | H | 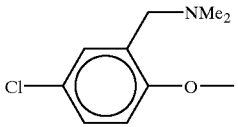 | MeSO₂— | H |
| 135 | H | H | t-Bu | MeO— | H |
| 136 | H | Br | i-Pr | MeSO₂— | H |
| 137 | CF₃ | H | H | H | H |
| 138 | H | H | F | CF₃ | H |
| 139 | H | Ph | H | CF₃ | H |
| 140 | H | H | 1-imidazolyl | CF₃ | H |
| 141 | H | H | cyclopentyl | CH₃CO— | H |
| 142 | H | H | t-butylmethyl | CH₃CO— | H |
| 143 | H | H | F | Br | H |
| 144 | H | Br | MeO— | Br | H |

-continued

| Example | R(1) = R(10) | R(2) = R(9) | R(3) = R(8) | R(4) = R(7) | R(5) = R(6) |
|---|---|---|---|---|---|
| 145 | NH$_2$ | Me | H | H | H |
| 146 | H | H | PhO— | CF$_3$ | H |
| 147 | H | H | cyclopentyl | CF$_3$ | H |
| 148 | H | H | cyclobutyl | MeSO$_2$— | H |
| 149 | H | Me | H | CF$_3$ | H |
| 150 | H | H | 4-CF$_3$-PhO | MeSO$_2$— | H |
| 151 | H | H | OH | t-butyl | H |
| 152 | H | Me$_2$N— | MeO— | Cl | H |
| 153 | H | H | isopropyl | CF$_3$ | H |
| 154 | H | CF$_3$ | H | H | F |
| 155 | H | H | MeO— | t-butyl | H |
| 156 | H | H | 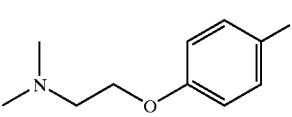 | MeSO$_2$— | H |
| 157 | H | Br | 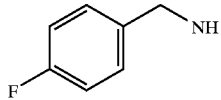 | Br | H |
| 158 | H | H | 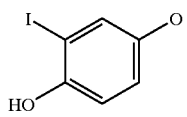 | MeSO$_2$— | H |
| 159 | H | H | 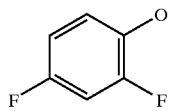 | CH$_3$CO— | H |
| 160 | H | H | 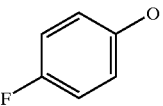 | CH$_3$CO— | H |
| 161 | H | H | 2-Methylpropyl | t-butyl | H |
| 162 | H | cyclopentyl | MeO— | CH$_3$CO— | H |
| 163 | H | H | isopropyl | CF$_3$CF$_2$ | H |
| 164 | H | H | 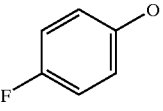 | CF$_3$SO$_2$ | H |
| 165 | H | CF$_3$ | H | H | Cl |
| 166 | H | H | 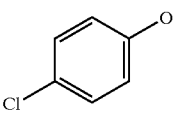 | CF$_3$ | H |
| 167 | H | H | Ph—C≡C | CF$_3$ | H |
| 168 | H | H | 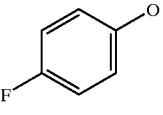 | CF$_3$ | H |
| 169 | H | F | H | CF$_3$ | H |

-continued

| Example | R(1) = R(10) | R(2) = R(9) | R(3) = R(8) | R(4) = R(7) | R(5) = R(6) |
|---|---|---|---|---|---|
| 170 | H | H | 3-chloro-4-fluoroanilino | MeSO₂— | H |
| 171 | H | H | isopropyl | t-butyl | H |
| 172 | H | H | n-buty | t-butyl | H |
| 173 | H | H | F | isopropyl | H |
| 174 | H | H | F | isobutyl | H |
| 175 | H | I | H | CF₃ | F |
| 176 | H | H | CF₃O— | Cl | H |
| 177 | NH₂ | H | Cl | H | Cl |
| 178 | H | H | 4-(2-dimethylaminoethyl)phenoxy | MeSO₂— | H |
| 179 | H | I | OH | t-butyl | H |
| 180 | H | H | isopropyl | CF₃SO₂ | H |
| 181 | H | H | 4-methoxyphenoxy | CF₃ | H |
| 182 | H | H | quinolin-6-yloxy | CF₃ | H |
| 183 | H | H | pyridin-3-yloxy | CF₃ | H |
| 184 | H | H | 4-methylimidazol-1-yl | CF₃ | H |
| 185 | H | H | 2-methylimidazol-1-yl | CF₃ | H |
| 186 | H | H | MeO— | CF₃ | H |
| 187 | H | H | H | isopropyl | H |
| 188 | H | H | isopropyl | MeS— | H |
| 189 | N,N'-bis(α-methylcinnamoyl)guanidine | | | | |
| 190 | N,N'-bis(3-trifluoromethylcinnamoyl)guanidine | | | | |

-continued
| Example | R(1) = R(10) | R(2) = R(9) | R(3) = R(8) | R(4) = R(7) | R(5) = R(6) |
|---|---|---|---|---|---|
| 191 | | | 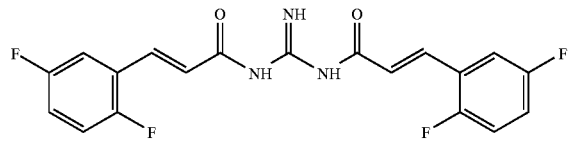 | | |
| 192 | | | 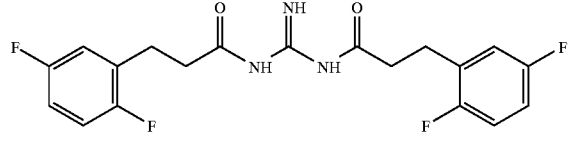 | | |
| 193 | | | 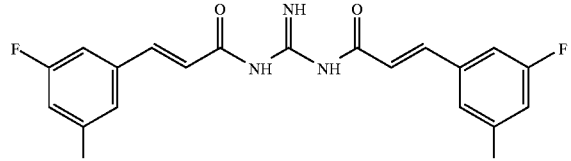 | | |
| 194 | | | 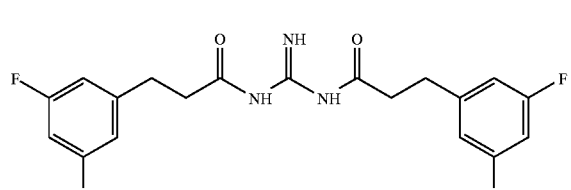 | | |
| 195 | | | 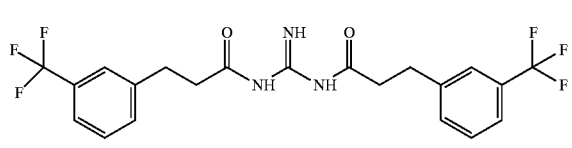 | | |
| 196 | | | 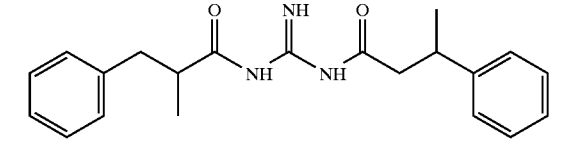 | | |
| 197 | | | 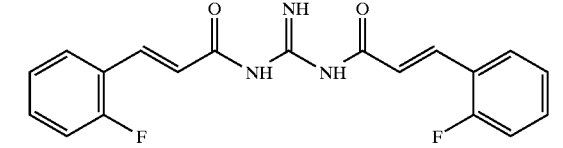 | | |
| 198 | | | 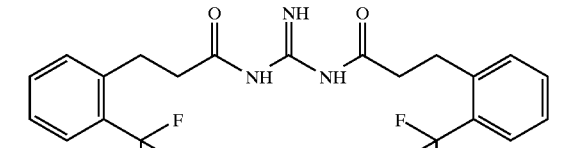 | | |
| 199 | | | 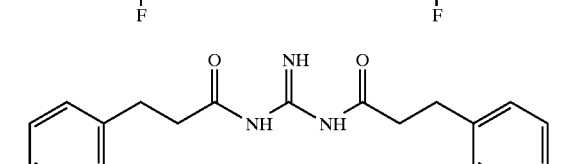 | | |

-continued

| Example | R(1) = R(10) | R(2) = R(9) | R(3) = R(8) | R(4) = R(7) | R(5) = R(6) |
|---|---|---|---|---|---|
| 200 | | | | | |
| 201 | | | | | |
| 202 | | | | | |
| 203 | | | | | |
| 204 | | | | | |

What is claimed is:

1. A diacyl-substituted guanidine of the formula I $$X(1)\underset{O}{\overset{}{\diagdown}}\underset{}{\overset{NH}{\diagup}}\underset{NH}{\overset{}{\diagdown}}\underset{O}{\overset{NH}{\diagup}}X(2) \quad\quad I$$

in which:

X(1) and X(2) are

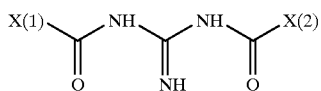

T1 is zero, 1, 2, 3 or 4,

R(A) and R(B) are, independently, hydrogen, F, Cl, Br, I, CN, OR(106), $(C_1-C_8)$-alkyl, $(C_3-C_8)$-cycloalkyl, $O_{zk}(CH_2)_{zl}C_{zm}F_{2zm}$, NR(107)R(108), phenyl or benzyl, where the aromatic radicals are not substituted or are substituted by 1–3 substituents selected from the group consisting of F, Cl, $CF_3$, methyl, methoxy and NR(109)R(110), R(109) and R(110) being hydrogen, $(C_1-C_4)$-alkyl or $(C_1-C_4)$-perfluoroalkyl, zl is zero, 1, 2, 3 or 4,
zk is zero or 1,
zm is 1, 2, 3, 4, 5, 6, 7 or 8, R(106) is hydrogen, $(C_1-C_8)$-alkyl, $(C_1-C_8)$-perfluoroalkyl, $(C_3-C_8)$-alkenyl, $(C_3-C_8)$-cycloalkyl, phenyl or benzyl, where the aromatic radicals are not substituted or are substituted by 1–3 substituents selected from the group consisting of F, Cl, $CF_3$, methyl, methoxy and NR(111)R(112), R(111) and R(112) being hydrogen, $(C_1-C_4)$-alkyl or $(C_1-C_4)$-perfluoroalkyl, R(107) and R(108) are, independently of each other, defined as R(106), or R(107) and R(108) are together 4 or 5 methylene groups of which one $CH_2$ group can be replaced by oxygen, S, NH, N—$CH_3$ or N-benzyl, or X(1) and X(2) are

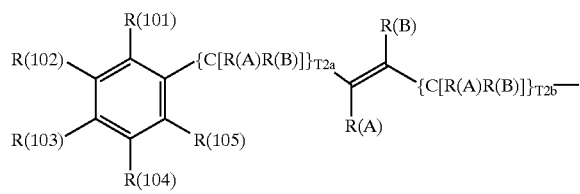

T2a and T2b are, independently of each other, zero, 1 or 2,
where the double bond can have the E or Z configuration;

or

X(1) and X(2) are

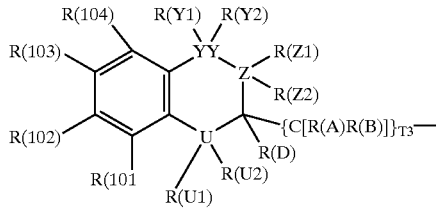

T3 is zero, 1 or 2,

U, YY and Z are, independently of each other, C or N,
where U, YY and Z can carry the following number of substituents:

| U, YY or Z | Bonded to a double bond in the ring | Number of permitted substituents |
| --- | --- | --- |
| C | yes | 1 |
| C | no | 2 |
| N | yes | 0 |
| N | no | 1 |

R(D) is hydrogen, $(C_1-C_8)$-alkyl or $(C_1-C_8)$-perfluoroalkyl, R(U1), R(U2), R(Y1), R(Y2), R(Z1) and R(Z2) are, independently of each other, hydrogen, F, Cl, Br, I, CN, OR(114), $(C_1-C_8)$-alkyl, $(C_3-C_8)$-cycloalkyl, $O_{zka}(CH_2)_{zla}C_{zma}F_{2zma+1}$, NR(115)R(116), phenyl or benzyl,
where the aromatic radicals are not substituted or are substituted by 1–3 substituents selected from the group consisting of F, Cl, $CF_3$, methyl, methoxy and NR(117)R(118),
R(117) and R(118) being
hydrogen, $(C_1-C_4)$-alkyl or $(C_1-C_4)$-perfluoroalkyl,
zka is zero or 1,
zla is zero, 1, 2, 3 or 4,
zma is 1, 2, 3, 4, 5, 6, 7 or 8,
R(114) is hydrogen, $(C_1-C_8)$-alkyl, $(C_1-C_8)$-perfluoroalkyl, $(C_3-C_8)$-alkenyl, $(C_3-C_8)$-cycloalkyl, phenyl or benzyl,
where the aromatic radicals are not substituted or are substituted by 1–3 substituents selected from the group consisting of F, Cl, $CF_3$, methyl, methoxy and NR(119)R(120),
R(119) and R(120) being
hydrogen, $(C_1-C_4)$-alkyl or $(C_1-C_4)$-perfluoroalkyl,
R(115) and R(116) are, independently of each other, defined as R(114), or R(115) and R(116)
are together 4 or 5 methylene groups of which one $CH_2$ group can be replaced by oxygen, S, NH, N—$CH_3$ or N-benzyl,
where, however, the constitution U is nitrogen (N), YY is nitrogen (N) and Z is carbon (C) is excepted, R(101), R(102), R(103), R(104) and R(105) are, independently of each other,
hydrogen, F, Cl, Br, I, —C≡N, $X_{zoa}$—$(CH_2)_{zpa}$—$(C_{zqa}F_{2zqa+1})$, R(110a)—$SO_{zbm}$, R(110b)R(110c)N—CO, R(111a)—CO— or R(112a)R(113a)N—$SO_2$—, where the perfluoroalkyl group is straight-chain or branched,
X is hydrogen, S or NR(114a),
zoa is zero or 1,
R(114a) being H or $(C_1-C_3)$-alkyl,
zbm is zero, 1 or 2,
zpa is zero, 1, 2, 3 or 4,
zqa is 1, 2, 3, 4, 5, 6, 7 or 8,
R(110a), R(110b), R(111a) and R(112a) are, independently,
$(C_1-C_8)$-alkyl, $(C_3-C_8)$-alkenyl, —$C_{zn}H_{2zn}$—R(115a) or $(C_1-C_8)$-perfluoroalkyl,
zn is zero, 1, 2, 3 or 4,
R(115a) is
$(C_3-C_8)$-cycloalkyl, phenyl, biphenylyl or naphthyl,
where the aromatic radicals are not substituted or are substituted by 1–3 substituents selected from the group consisting of F, Cl, $CF_3$, methyl, methoxy and NR(116a)R(117a),
R(116a) and R(117a) being
hydrogen, $(C_1-C_4)$-perfluoroalkyl or $(C_1-C_4)$-alkyl, or R(110b), R(111a) and R(112a) are also hydrogen, R(110c) and R(113a) are, independently,
hydrogen, $(C_1-C_4)$-perfluoroalkyl or $(C_1-C_4)$-alkyl, or R(110b) and R(110c) and also R(112a) and R(113a) are together 4 or 5 methylene groups of which one $CH_2$ group can be replaced by oxygen, sulfur, NH, N—$CH_3$ or N-benzyl, or R(101), R(102), R(103), R(104) and R(105) are, independently of each other,
$(C_1-C_8)$-alkyl, —$C_{zal}H_{2zal}$R(118a) or $(C_3-C_8)$-alkenyl,
zal is zero, 1, 2, 3 or 4,
R(118a) is
$(C_3-C_8)$-cycloalkyl, phenyl, biphenylyl or naphthyl,
where the aromatic radicals are not substituted or are substituted by 1–3 substituents from the group consisting of F, Cl, $CF_3$, methyl, methoxy or NR(119a)R(119b),
R(119a) and R(119b) being
hydrogen, $(C_1-C_4)$-alkyl or $(C_1-C_4)$-perfluoroalkyl, or R(101), R(102), R(103), R(104) and R(105) are, independently of each other,
$(C_1-C_9)$-heteroaryl which is linked via C or N and which is unsubstituted or is substituted by 1–3 substituents from the group consisting of F, Cl, $CF_3$, $CH_3$, methoxy, hydroxyl, amino, methylamino and dimethylamino, or R(101), R(102), R(103), R(104) and R(105) are, independently of each other,
—C≡C—R(193),
R(193) is
phenyl which is not substituted or is substituted by 1–3 substituents from the group consisting of F, Cl, $CF_3$, methyl, methoxy or NR(194)R(195), R(194) and R(195) being hydrogen or $CH_3$, or R(101), R(102), R(103), R(104) and R(105) are, independently of each other, —Y-para-$C_6H_4$—$(CO)_{zh}$—$(CHOH)_{zi}$—$(CH_2)_{zj}$—$(CHOH)_{zk}$—R(123), —Y-meta-$C_6H_4$—$(CO)_{zad}$—$(CHOH)_{zae}$—$(CH_2)_{zaf}$—$(CHOH)_{zag}$—R(124)

or

—Y-ortho-C6H$_4$—$(CO)_{zah}$—$(CHOH)_{zao}$—$(CH_2)_{zap}$—$(CHOH)_{zak}$—R(125), Y is oxygen, —S— or —NR(122d)—, zh, zad and zah are, independently,
  zero or 1,
zi, zj, zk, zae, zaf, zag, zao, zap and zak are, independently,
  zero, 1, 2, 3 or 4,
where, however, in each case,
  zh, zi and zk are not simultaneously zero,
  zad, zae and zag are not simultaneously zero,
  zah, zao and zak are not simultaneously zero,
  R(123), R(124), R(125) and R(122d) are, independently, hydrogen or $(C_1-C_3)$-alkyl, or R(101), R(102), R(103), R(104) and R(105) are, independently of each other,
  SR(129), —OR(130), —NR(131)R(132) or —CR(133)R(134)R(135),
  R(129), R(130), R(131) and R(133), are, independently,
    —$C_{zab}H_{2zab}$—$(C_1-C_9)$-heteroaryl which is unsubstituted or is substituted by 1–3 substituents from the group consisting of F, Cl, $CF_3$, $CH_3$, methoxy, hydroxyl, amino, methylamino and dimethylamino,
    zab is zero, 1 or 2,
  R(132), R(134) and R(135) are, independently of each other,
    defined as R(129), or hydrogen, $(C_1-C_4)$-alkyl or $(C_1-C_4)$-perfluoroalkyl, or R(101), R(102), R(103), R(104) and R(105) are, independently of each other,
  —W-para-$(C_6H_4)$—R(196), —W-meta-$(C_6H_4)$—R(197) or —W-ortho-$(C_6H_4)$—R(198),
  R(196), R(197) and R(198) are, independently,
    $(C_1-C_9)$-heteroaryl which is linked via C or N and which is unsubstituted or is substituted by 1 to 3 substituents from the group consisting of F, Cl, $CF_3$, $CH_3$, methoxy, hydroxyl, amino, methylamino, dimethylamino and benzyl,
  W is oxygen, S or NR(136)—,
  R(136) being hydrogen or $(C_1-C_4)$-alkyl, or R(101), R(102), R(103), R(104) and R(105) are, independently of each other,
  R(146)X(1a)—,
  X(1a) is oxygen, S, NR(147), (D=O)A— or NR(148)C=MN(*)R(149)—,
  M is oxygen or sulfur,
  A is oxygen or NR(150), and
  D is C or SO,
  R(146) is $(C_1-C8)$-alkyl, $(C_3-C_8)$-alkenyl, $(CH2)_{zbz}$—$C_{zdz}F_{2zdz+1}$ or —$C_{zxa}H_{2zxa}$—R(151),
  zbz is zero or 1,
  zdz is 1, 2, 3, 4, 5, 6 or 7,
  zxa is zero, 1, 2, 3 or 4, R(151) is
  $(C_3-C_8)$-cycloalkyl, phenyl, biphenylyl or naphthyl, where the aromatic radicals are not substituted or are substituted by 1–3 substituents from the group consisting of F, Cl, $CF_3$, methyl, methoxy and NR(152)R(153),
  R(152) and R(153) being
    hydrogen, $(C_1-C_4)$-alkyl or $(C_1-C_4)$-perfluoroalkyl,
  R(147), R(148) and R(150) are, independently,
    hydrogen, $(C_1-C_4)$-alkyl or $(C_1-C_4)$-perfluoroalkyl,
  R(149) is defined as R(146), or R(146) and R(147), or R(146) and R(148), respectively, are together 4 or 5 methylene groups of which one $CH_2$ group can be replaced by oxygen, sulfur, NH, N—$CH_3$ or N-benzyl, where A and $N^{(*)}$ are bonded to the phenyl nucleus of the alkanoyl parent substance, or R(101), R(102), R(103), R(104) and R(105) are, independently of each other,
  —SR(164), —OR(165), —NHR(166), —NR(167)R(168), —CHR(169)R(170), —CR(154)R(155)OH, —C=CR(156), —CR(158)=CR(157) or —[CR(159)R(160)]$_{zu}$—(C=O)—[CR(161)R(162)]$_{zv}$—R(163),
  R(164), R(165), R(166), R(167) and R(169) are identical or different and are
    —$(CH_2)_{zy}$—$(CHOH)_{zz}$—$(CH_2)_{zaa}$—$(CHOH)_{zt}$—R(171)
  or
    —$(CH_2)_{zab}$—O—$(CH_2$–$CH_2O)_{zac}$—R(172), R(171) and R(172) being hydrogen or methyl,
  zu is 1, 2, 3 or 4,
  zv is zero, 1, 2, 3 or 4,
  zy, zz, zaa, zab and zac are identical or different and are
    zero, 1, 2, 3 or 4,
  zt is 1, 2, 3 or 4,
  R(168), R(170), R(154) and R(155) are identical or different and are
    hydrogen or $(C_1-C_6)$-alkyl,
  or
  R(169) and R(170), or R(154) and R(155), respectively, are, together with the carbon atom carrying them, a $(C_3-C_8)$-cycloalkyl,
  R(163)
    is hydrogen, $(C_1-C_6)$-alkyl, $(C_3-C_8)$-cycloalkyl or —$C_{zeb}H_{2zeb}$—R(173),
    zeb is zero, 1, 2, 3 or 4,
  R(156), R(157) and R(173) are, independently,
    phenyl which is unsubstituted or is substituted by 1–3 substituents from the group consisting of F, Cl, $CF_3$, methyl, methoxy and NR(174)R(175),
    R(174) and R(175) being
      hydrogen or $(C_1-C_4)$-alkyl,
  or
  R(156), R(157) and R(173) are, independently,
    $(C_1-C_9)$-heteroaryl which is unsubstituted or is substituted as phenyl,
  R(158), R(159), R(160), R(161) and R(162) are hydrogen or methyl, or R(101), R(102), R(103), R(104) and R(105) are, independently of each other,

R(176)—NH—SO₂—,

R(176) is R(177)R(178)N—(C=Y')—,

Y' is oxygen, S or N—R(179),

R(177) and R(178) are identical or different and are hydrogen, (C₁–C₈)-alkyl, (C₃–C₆)-alkenyl or —C$_{zfa}$H$_{2zfa}$—R(180), zfa is zero, 1, 2, 3 or 4, R(180) is (C₅–C₇)-cycloalkyl or phenyl which is unsubstituted or substituted by 1–3 substituents from the group consisting of F, Cl, CF₃, methoxy or (C₁–C₄)-alkyl, or R(177) and R(178)

are together 4 or 5 methylene groups of which one CH₂ group can be replaced by oxygen, sulfur, NH, N—CH₃ or N-benzyl, R(179) is defined as R(177) or is amidine, or R(101), R(102), R(103), R(104) and R(105) are, independently of each other, here, however, the following compounds are excepted:

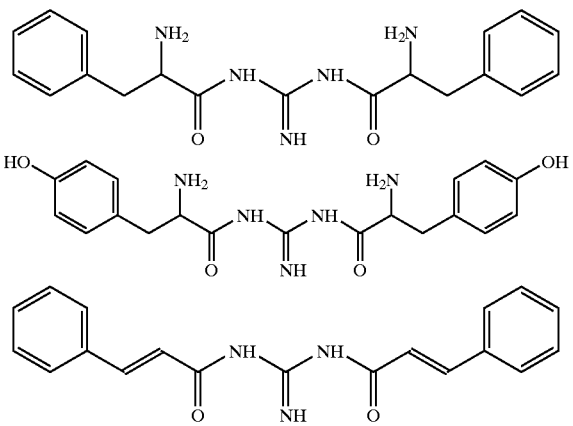

and where, additionally, the compounds are excepted in which the radicals R(1) to R(5) are combined as follows:

| R(101) [X(1)] | R(102) [X(1)] | R(103) [X(1)] | R(104) [X(1)] | R(105) [X(1)] | R(105) [X(2)] | R(104) [X(2)] | R(103) [X(2)] | R(102) [X(2)] | R(101) [X(2)] |
|---|---|---|---|---|---|---|---|---|---|
| H | Cl | Cl | H | H | H | H | Cl | Cl | H |
| H | H | NH₂ | H | H | H | H | NH₂ | H | H |
| H | H | H | H | H | H | H | H | H | H |
| Cl | H | H | H | H | H | H | H | H | Cl |
| H | H | Cl | H | H | H | H | Cl | H | H |
| H | H | CH₃ | H | H | H | H | CH₃ | H | H |
| H | H | NH₂ | H | H | H | H | H | H | H |
| H | H | Cl | H | H | H | H | H | H | H |
| H | H | CH₃ | H | H | H | H | H | H | H |

OR(184b), SR(184c) or —C$_{znx}$H$_{2znx}$—R(184d), znx is zero, 1, 2, 3 or 4,

R(184d)

is (C₃–C₇)-cycloalkyl or phenyl which is not substituted or is substituted by 1–3 substituents from the group consisting of F, Cl, CF₃, methyl, methoxy and NR(116k)R(117k), R(116k) and R(117k) being hydrogen or (C₁–C₄)-alkyl, R(184a), R(184b), R(184c) and R(185) are, independently of each other, hydrogen, (C₁–C₈)-alkyl, (C₁–C₈)-perfluoroalkyl or (CH₂)$_{zao}$—R(184g), zao is zero, 1, 2, 3 or 4, 184g is (C₃–C₇)-cycloalkyl or phenyl which is not substituted or is substituted by 1–3 substituents from the group consisting of F, Cl, CF₃, methyl, methoxy and NR(184u)R(184v), R(184u) and R(184v) being hydrogen or (C₁–C₄)-alkyl, or R(184a) and R(185) are together 4 or 5 methylene groups of which one CH₂ group can be replaced by oxygen, sulfur, NH, N—CH₃ or N-benzyl, and also pharmaceutically tolerated salts thereof, 2. A compound of the formula I as claimed in claim 1, wherein X(1) is identical to X(2)

and wherein the remaining substituents are defined as in claim 1.

3. A compound of the formula I as claimed in claim 1, wherein:

X(1) and X(2) are

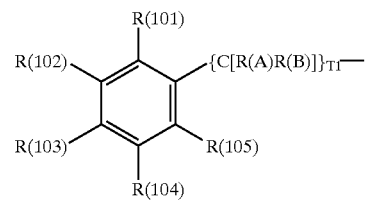

T1 is zero or 2,

R(A) and R(B) are, independently, hydrogen, F, Cl, CN, OR(106), (C₁–C₄)-alkyl, (C₅–C₆)-cycloalkyl, CF₃ or NR(107)R(108),

R(106)

is hydrogen, (C₁–C₄)-alkyl, CF₃, phenyl or benzyl, where the aromatic radicals are not substituted or are substituted by 1–3 substituents selected from the group consisting of F, Cl, CF₃, methyl, methoxy and NR(111)R(112), R(111) and R(112) being hydrogen, CH₃ or CF₃, R(107) and R(108) are, independently of each other, defined as R(106), or
R(107) and R(108) are together 4 or 5 methylene groups of which one $CH_2$ group can be replaced by oxygen, S, NH, N—$CH_3$ or N-benzyl,
or
X(1) is

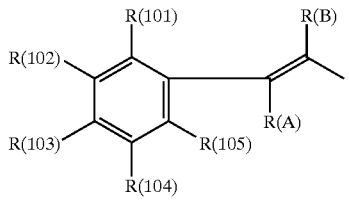

where the double bond can be in the E or Z configuration,
or
X (1) is

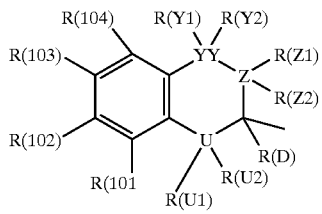

U, YY and Z are, independently of each other,
C or N;
with, however, the restriction that only one of the positions U, YY and Z can be nitrogen;
where
U, YY and Z can carry the following number of substituents:

| U, YY or Z | Bonded to a double bond in the ring | Number of permitted substituents |
|---|---|---|
| C | yes | 1 |
| C | no | 2 |
| N | yes | 0 |
| N | no | 1 |

R(D) is hydrogen,
R(U1), R(U2), R(Y1), R(Y2), R(Z1) and R(Z2) are, independently of each other,
hydrogen, F, Cl, CN, OR(114), $CH_3$, $CF_3$ or NR(115)R(116),
R(114)
is hydrogen, $(C_1-C_4)$-alkyl, $CF_3$, phenyl or benzyl, where the aromatic radicals are not substituted or are substituted by 1–3 substituents selected from the group consisting of F, Cl, $CF_3$methyl, methoxy and NR(119)R(120),
R(119) and R(120) being hydrogen, $C_3$ or $CF_3$,
R(115) and R(116) are, independently of each other, defined as R(114),
or
R(115) and R(116)
are together 4 or 5 methylene groups of which one $CH_2$ group can be replaced by oxygen, S, NH, N—$CH_3$ or N-benzyl, R(101)
is hydrogen, F, Cl, $CH_3$, OH, $NH_2$ or $CF_3$,
R(102)
is hydrogen, F, Cl, Br, —C≡N, —$C_{zqa}F_{2zqa}CF_3$, R(110a)—$SO_2$, R(110b)R(110c)N—CO—, R(111a)—CO—or R(112a)R(113a)N—$SO_2$—,
R(110a), R(110b), R(111a) and R(112a) are, independently,
$(C_1-C_4)$-alkyl, $(C_3-C_4)$-alkenyl, —$C_{zn}H_{2zn}$—R(115a) or $CF_3$,
zn is zero or 1,
zqa is zero, 1, 2, 3, 4 or 5,
R(115a)
is $(C_3-C_6)$-cycloalkyl or phenyl
which is not substituted or is substituted by 1–2 substituents from the group consisting of F, Cl, $CF_3$, methyl, methoxy and NR(116a)R(117a),
R(116a) and R(117a)
being hydrogen or methyl,
or
R(110b), R(111a) and R(112a) are also hydrogen, R(110c) and R(113a) are, independently, hydrogen or methyl,
R(103)
is —Y-para-$C_6H_4$—$(CO)_{zh}$—$(CHOH)_{zi}$—$(CH_2)_{zj}$—$(CHOH)_{zk}$—R(123),
—Y-meta-$C_6H_4$—$(CO)_{zad}$—$(CHOH)_{zae}$—$(CH_2)_{zaf}$—$(CHOH)_{zag}$—R(124) or
—Y-ortho-$C6H_4$—$(CO)_{zah}$—$(CHOH)_{zao}$—$(CH_2)_{zap}$—$(CHOH)_{zak}$—R(125),
Y is oxygen, S or —NR(83),
R(123), R(124), R(125) and R(83) are, independently, hydrogen or methyl,
zh, zad and zah are, independently,
zero or 1,
zi, zk, zae, zag, zao and zak are, independently,
zero, 1, 2 or 3,
zj, zaf and zap are, independently,
zero or 1,
where, however, in each case, zh, zi and zk are not simultaneously zero,
zad, zae and zag are not simultaneously zero and
zah, zao and zak are not simultaneously zero,
or
R(103) is hydrogen, F, Cl, Br, CN, $(C_1-C_8)$-alkyl, $CF_3$, $(C_3-C_8)$-alkenyl or —$C_{zal}H_{2zal}$R(118a),
zal is zero, 1 or 2,
R(118a) is $(C_3-C_6)$-cycloalkyl or phenyl
which is not substituted or is substituted by 1–2 substituents selected from the group consisting of F, Cl, $CF_3$, methyl, methoxy and NR(119a)R(119b),
R(119a) and R(119b) being
hydrogen or $CH_3$,
or
R(103)
is $(C_1-C_9)$-heteroaryl
which is linked via C or N and which is unsubstituted or is substituted by 1–2 substituents from the group consisting of F, Cl, $CF_3$, $CH_3$, methoxy, hydroxyl, amino, methylamino and dimethylamino,
or
R(103)
is —W-para-$(C_6H_4)$—R(196), —W-meta-$(C_6H_4)$—R(197) or —W-ortho-$(C_6H_4)$—R(198), R(196), R(197) and R(198) are, independently, pyrrolyl, imidazolyl, pyrazolyl or pyridyl
which in each case is unsubstituted or substituted by 1 to 2 radicals selected from the group consisting of F, Cl, $CF_3$, $CH_3$, methoxy, dimethylamino and benzyl,
W is oxygen, —S— or NR(136)—,
R(136) being hydrogen or methyl, or R(103) is
—SR(129), —OR(130), —NR(131)R(132) or —CR(133)R(134)R(135),
R(129), R(130), R(131) and R(133) are, independently of each other,
—$C_{zab}H_{2zab}$—($C_1$–$C_9$)-heteroaryl
which is unsubstituted or substituted by 1–2 substituents selected from the group consisting of F, Cl, $CF_3$, $CH_3$, methoxy, hydroxyl, amino, methylamino and dimethylamino,
zab is zero or 1,
R(132), R(134) and R(135) are, independently of each other,
hydrogen or $CH_3$, or R(103) is
R(110a)—$SO_2$ or R(112a)R(113a)N—$SO_2$—,
R(110a) is
($C_1$–$C_4$)-alkyl, $CF_3$, ($C_3$–$C_4$)-alkenyl or —$C_{zn}H_{2zn}$—R(115a),
zn is zero or 1,
R(115a) is
($C_3$–$C_6$)-cycloalkyl or phenyl
which is not substituted or is substituted by 1–2 substituents selected from the group consisting of F, Cl, $CF_3$, methyl, methoxy and NR(116a)R(117a),
R(116a) and R(117a) being
hydrogen or $CH_3$,
R(112a) is
hydrogen, ($C_1$–$C_4$)-alkyl, $CF_3$, ($C_3$–$C_4$)-alkenyl or —$C_{za}H_{2za}$—R(115a),
za is zero or 1,
R(115a) is
($C_3$–$C_6$)-cycloalkyl or phenyl
which is not substituted or is substituted by 1–2 substituents selected from the group consisting of F, Cl, $CF_3$, methyl, methoxy and NR(116a)R(117a),
R(116a) and R(117a) being
hydrogen or $CH_3$,
R(113a) is
hydrogen or $CH_3$, or R(112a) and R(113a) are together 4 or 5 methylene groups of which one $CH_2$ group can be replaced by oxygen, S, NH, N—$CH_3$ or N-benzyl, or R(103) is
R(146)X(1a)—,
X(1a) is oxygen, S, NR(147), (C=O)A— or NR(148)C=MN$^{(*)}$R(149)—,
M is oxygen, and
A is oxygen or NR(150),
R(146) and R(147) are, independently, hydrogen, ($C_1$–$C_6$)-alkyl, ($C_3$–$C_4$)-alkenyl,
$(CH_2)_{zbz}C_{zdz}F_{2zdz+1}$ or $C_{zxa}H_{2zxa}$—R(151),
zbz is zero or 1,
zdz is 1, 2, 3, 4, 5, 6 or 7,
zxa is zero or 1,
R(151)
is ($C_3$–$C_6$)-cycloalkyl or phenyl which is not substituted or is substituted by 1–2 substituents selected from the group consisting of F, Cl, $CF_3$, methyl, methoxy or NR(152)R(153),
R(152) and R(153) being
hydrogen or $CH_3$,
R(148)
is hydrogen or ($C_1$–$C_4$)-alkyl,
R(149) is defined as R(146), or R(146) and R(147), or R(146) and R(148), respectively, are together 4 or 5 methylene groups of which one $CH_2$ group can be replaced by oxygen, S, NH, N—$CH_3$ or N-benzyl, where A and N$^{(*)}$ are bonded to the phenyl nucleus of the benzoylguanidine parent substance, or R(103)
is —SR(164), —OR(165), —NHR(166), —NR(167)R(168), —CHR(169)R(170), —[CR(154)R(155)OH], —C≡CR(156), —CR(158)=CR(157) or
—[CR(159)R(160a)]$_{zu}$—(CO)—[CR(161)R(162)]$_{zv}$—R(163), R(164), R(165), R(166), R(167) and R(169) are identical or different and are
—$(CH_2)_{zy}$—$(CHOH)_{zz}$—$(CH_2)_{zaa}$—$(CHOH)_{zt}$—R(171) or
—$(CH_2)_{zab}$—O—$(CH_2-CH_2O)_{zac}$—R(172),
R(171) and R(172) are hydrogen or methyl,
zu is 1 or 2,
zv is zero, 1 or 2,
zy, zz, zaa, zab and zac are identical or different and are zero, 1 or 2,
zt is 1, 2 or 3,
R(168), R(170), R(154) and R(155) are identical or different and are
hydrogen or methyl, or R(169) and R(170), or R(154) and R(155), respectively, together with the carbon atom carrying them, are a ($C_3$–$C_6$)-cycloalkyl,
R(163) is
hydrogen, ($C_1$–$C_4$)-alkyl, ($C_3$–$C_6$)-cycloalkyl or —$C_{zeb}H_{2zeb}$—R(173),
zeb is zero, 1 or 2,
R(156), R(157) and R(173) are, independently of each other,
phenyl which is unsubstituted or is substituted by 1–2 substituents selected from the group consisting of F, Cl, $CF_3$, methyl, methoxy and NR(174) R(175),
R(174) and R(175) being
hydrogen or $CH_3$, or R(156), R(157) and R(173) are, independently of each other,
($C_1$–$C_9$)-heteroaryl which is unsubstituted or is substituted as phenyl,
R(158), R(159), R(160), R(161) and R(162)
are hydrogen or methyl, or R(103)
  is R(176)—NH—SO$_2$—,
  R(176)
  is R(177)R(178)N—(C=Y')—,
  Y' is oxygen, S or N—R(179),
  R(177) and R(178) are identical or different and are hydrogen, (C$_1$–C$_4$)-alkyl, (C$_3$–C$_4$)-alkenyl or —C$_{zfa}$H$_{2zfa}$—R(180),
  zfa is zero or 1,
    R(180)
    is (C$_5$–C$_7$)-cycloalkyl or phenyl which is unsubstituted or substituted by 1–2 substituents selected from the group consisting of F, Cl, CF$_3$, methoxy or methyl,
  or
  R(177) and R(178) are together 4 or 5 methylene groups of which one CH$_2$ group can be replaced by oxygen, S, NH, N—CH$_3$ or N-benzyl,
    R(179) is defined as R(177),
R(104)
  is hydrogen, CF$_3$ (C$_1$–C$_8$)-alkyl or —C$_{zal}$H$_{2zal}$R($^{118}$a),
  zal is zero or 1,
    R(118a)
    is (c$_{3-C6}$)-cycloalkyl or phenyl which is not substituted or is substituted by 1–2 substituents selected from the group consisting of F, Cl, CF$_3$, methyl, methoxy and NR(119a)R(119b),
      R(119a) and R(119b) being hydrogen or CH$_3$,
or
R(104)
  is quinolyl, isoquinolyl, pyrrolyl, pyridyl or imidazolyl which are linked via C or N and which are unsubstituted or substituted by 1–2 substituents selected from the group consisting of F, Cl, CF$_3$, CH$_3$, methoxy, hydroxyl, amino, methylamino and dimethylamino,
or
R(104)
  is R(110a)—SO$_2$ or R(112a)R(113a)N—SO$_2$—,
  R(110a)
  is (C$_1$–C$_4$)-alkyl or CF$_3$,
  R(112a)
  is hydrogen, (C$_1$–C$_4$)-alkyl, CF$_3$ or —C$_{za}$H$_{2za}$—R(115),
  za is zero or 1,
    R(115a)
    is phenyl which is not substituted or is substituted by 1–2 substituents selected from the group consisting of F, Cl, CF$_3$, methyl, methoxy and NR(116a)R(117a),
      R(116a) and R(117a) being hydrogen or CH$_3$,
  R(113a)
  is hydrogen or CH$_3$,
or
R(104)
  is —C≡CR(193),
  R(193)
  is phenyl which is unsubstituted or substituted by 1–2 substituents selected from the group consisting of F, Cl, CF$_3$, methyl, methoxy and NR(194)R(195),
    R(194) and R(195) being hydrogen or CH$_{31}$, R(105)
  is hydrogen.

4. A process for preparing a compound I as claimed in claim 1, wherein
  a) two equivalents of the compounds of the formula II are reacted with one equivalent of the guanidine,

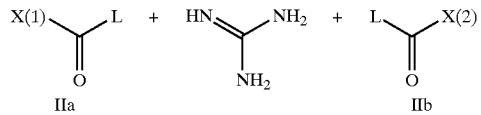

where X(1) and X(2) have the given meaning and L is a leaving group which can readily be substituted nucleophilically, or
  b) a compound of the formula IIa

is reacted with a compound of the formula III

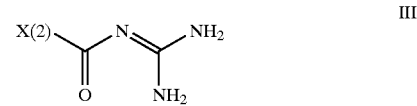

with the participation of a base, where X(1) and X(2) have the given meaning and L is a leaving group which can readily be substituted nucleophilically,
  and wherein conversion takes place, where appropriate, into a pharmaceutically tolerated salt.

5. A method of treating arrhythmias, which comprises administering to a host in need of said treatment an effective amount of a compound of the formula I as claimed in claim 1.

6. A pharmaceutical composition for the treatment of arrhythmias, which comprises a compound of formula I as claimed in claim 1 together with a pharmaceutically acceptable auxiliary substance.

7. A method of treating or preventing cardiac infarct, which comprises administering to a host in need of said treatment an effective amount of a compound of the formula I as claimed in claim 1.

8. A method of treating or preventing angina pectoris, which comprises administering to a host in need of said treatment an effective amount of a compound of the formula I as claimed in claim 1.

9. A method of treating or preventing ischemic conditions of the heart, which comprises administering to a host in need of said treatment an effective amount of a compound of the formula I as claimed in claim 1.

10. A method of treating or preventing ischemic conditions of the peripheral and central nervous systems and of stroke, which comprises administering to a host in need of said treatment an effective amount of a compound of the formula I as claimed in claim 1.

11. A method of treating or preventing ischemic conditions of the peripheral organs and limbs, which comprises administering to a host in need of said treatment an effective amount of a compound of the formula I as claimed in claim 1.

12. A method of treating shock conditions, which comprises administering to a host in need of said treatment an effective amount of a compound of the formula I as claimed in claim 1.

13. A pharmaceutical composition for use in surgical operations and organ transplants, which comprises a compound of formula I as claimed in claim 1 and a pharmaceutically acceptable auxiliary substance.

14. A method of preventing and storing transplants for surgical procedures, which comprises treating said transplants with an effective amount of a compound of formula I as claimed in claim 1.

15. A method of treating diseases in which cell proliferation is a primary or secondary cause, which comprises administering to a host in need of said treatment an effective amount of a compound of the formula I as claimed in claim 1.

16. The method according to claim 15, wherein the disease in which cell proliferation is a primary or secondary cause, is atherosclerosis, a late complication of diabetes, cancer, a fibrotic disease, or prostate hyperplasia.

17. The method according to claim 16, wherein the fibrotic disease is pulmonary fibrosis, hepatic fibrosis, or renal fibrosis.

18. A diagnostic aid for inhibiting the Na+/H+ exchanger and for diagnosing hypertension and proliferative diseases, which comprises an effective amount of a compound of formula I as claimed in claim 1.

19. A pharmaceutical composition for the treatment of cardiac infarct, angina pectoris, ischemic conditions of the heart, the peripheral and central nervous systems, the peripheral organs and limbs, of stroke, of shock conditions, and of diseases in which cell proliferation is a primary or secondary cause, which comprises an effective amount of a compound of formula I as claimed in claim 1 together with a pharmaceutically acceptable auxiliary substance.

* * * * *

UNITED STATES PATENT AND TRADEMARK OFFICE
CERTIFICATE OF CORRECTION

PATENT NO. : 6,436,999 B1
DATED : August 20, 2002
INVENTOR(S) : Kleeman et al.

It is certified that error appears in the above-identified patent and that said Letters Patent is hereby corrected as shown below:

Column 49,
Line 66, "$O_{zk}(CH_2)_{zl}C_{zm}F_{2zm}$" should read -- $O_{zk}(CH_2)_{zl}C_{zm}F_{2zm+1}$ --.

Column 53,
Line 21, after "ortho", "-C6H$_4$—" should read -- -$C_6H_4$- --.

Column 54,
Line 5, "MN(*)" should read -- $MN^{(*)}$ --.
Line 9, "($C_1$-C8)-alkyl" should read -- ($C_1$-$C_8$)-alkyl --.
Line 9, "(CH2)$_{zbz}$—" should read -- $(CH_2)_{zbz}$— --.

Column 55,
Line 59, "here" should read -- where --.

Column 57,
Line 24, "X (1)" should read -- X(1) --.
Line 63, "$CF_3$methyl" should read -- $CF_3$, methyl --.
Line 64, "$C_3$" should read -- $CH_3$ --.

Column 58,
Line 12, "CO-or" should read -- CO- or --.
Line 36, after "ortho", "-C6H$_4$—" should read -- -$C_6H_4$- --.

Column 59,
Line 13, "oxygen,-" should read -- oxygen, - --.

UNITED STATES PATENT AND TRADEMARK OFFICE
CERTIFICATE OF CORRECTION

PATENT NO. : 6,436,999 B1
DATED : August 20, 2002
INVENTOR(S) : Kleeman et al.

It is certified that error appears in the above-identified patent and that said Letters Patent is hereby corrected as shown below:

Column 61,
Line 28, "R($^{118}$a)" should read -- R(118a) --.
Line 31, "(c$_3$-$_{C6}$)-cycloalkyl" should read -- (C$_3$-C$_6$)-cycloalkyl --.

Column 62,
Line 2, "CH$_{31}$," should read -- CH$_3$, --.

Signed and Sealed this

Twenty-ninth Day of October, 2002

Attest:

Attesting Officer

JAMES E. ROGAN
*Director of the United States Patent and Trademark Office*